US008642644B2

(12) United States Patent
Toone et al.

(10) Patent No.: US 8,642,644 B2
(45) Date of Patent: Feb. 4, 2014

(54) OPHTHAMOLOGICAL DRUGS

(75) Inventors: Eric J. Toone, Durham, NC (US); David L. Epstein, Bahama, NC (US); Pratap Challa, Durham, NC (US); Phillip W. Snyder, Cambridge, MA (US); Xin Chen, Chapell Hill, NC (US); Mitchell A. deLong, Raleigh, NC (US)

(73) Assignee: Duke University, Durham, NC (US)

( * ) Notice: Subject to any disclaimer, the term of this patent is extended or adjusted under 35 U.S.C. 154(b) by 448 days.

(21) Appl. No.: 12/511,861

(22) Filed: Jul. 29, 2009

(65) Prior Publication Data
US 2009/0318542 A1 Dec. 24, 2009

Related U.S. Application Data

(62) Division of application No. 11/255,478, filed on Oct. 21, 2005, now abandoned.

(60) Provisional application No. 60/620,320, filed on Oct. 21, 2004.

(51) Int. Cl.
A01N 43/12 (2006.01)
A01N 43/06 (2006.01)
A01N 37/10 (2006.01)
A61K 9/00 (2006.01)

(52) U.S. Cl.
USPC ........... 514/443; 514/445; 514/545; 514/547; 424/400

(58) Field of Classification Search
None
See application file for complete search history.

(56) References Cited

U.S. PATENT DOCUMENTS

| | | | |
|---|---|---|---|
| 3,746,728 A | 7/1973 | Weisbach | |
| 3,776,938 A | 12/1973 | Bergstrom et al. | |
| 3,882,241 A | 5/1975 | Phariss | |
| 4,094,968 A | 6/1978 | Hodson et al. | |
| 4,198,429 A | 4/1980 | Bartmann et al. | |
| 4,310,512 A | 1/1982 | Schleppnik | |
| 4,481,191 A | 11/1984 | Wei et al. | |
| 4,500,523 A | 2/1985 | Nathanielsz | |
| 4,757,089 A | 7/1988 | Epstein | |
| 5,061,714 A | 10/1991 | Tadokoro et al. | |
| 5,073,641 A | 12/1991 | Bundgaard et al. | |
| 5,458,883 A | 10/1995 | Epstein | |
| 5,565,434 A | 10/1996 | Barfknecht et al. | |
| 5,770,759 A | 6/1998 | Ueno et al. | |
| 5,837,723 A | 11/1998 | Watanabe | |
| 5,863,948 A | 1/1999 | Epstein et al. | |
| 5,898,038 A | 4/1999 | Yallampalli et al. | |
| 5,977,173 A | 11/1999 | Wos et al. | |
| 6,048,895 A | 4/2000 | Wos et al. | |
| 6,051,576 A | 4/2000 | Ashton et al. | |
| 6,066,740 A | 5/2000 | Godlewski et al. | |
| 6,107,338 A | 8/2000 | Wos et al. | |
| 6,126,957 A | 10/2000 | Epstein | |
| 6,372,730 B1 | 4/2002 | DeLong et al. | |
| 6,410,780 B1 | 6/2002 | deLong et al. | |
| 6,444,840 B1 | 9/2002 | deLong et al. | |
| 6,451,859 B1 | 9/2002 | deLong et al. | |
| 6,534,082 B1 | 3/2003 | Epstein | |
| 6,548,535 B2 | 4/2003 | Garcia et al. | |
| 6,586,463 B2 | 7/2003 | DeLong et al. | |
| 6,716,876 B2 | 4/2004 | Burk | |
| 6,841,536 B2 | 1/2005 | Roberts et al. | |
| 6,977,260 B2 | 12/2005 | Old et al. | |
| 6,988,994 B2 | 1/2006 | Rapoport et al. | |
| 7,015,243 B2 | 3/2006 | Old et al. | |
| 7,022,726 B2 | 4/2006 | Burk et al. | |
| 2001/0047025 A1 | 11/2001 | Garcia et al. | |
| 2002/0013294 A1 | 1/2002 | DeLong et al. | |
| 2002/0037913 A1 | 3/2002 | deLong et al. | |
| 2002/0037914 A1 | 3/2002 | delong et al. | |
| 2002/0146439 A1 | 10/2002 | deLong et al. | |
| 2002/0172693 A1 | 11/2002 | DeLong et al. | |
| 2003/0118528 A1 | 6/2003 | Walters et al. | |
| 2003/0191173 A1 | 10/2003 | Garcia et al. | |
| 2004/0131648 A1 | 7/2004 | deLong et al. | |
| 2004/0157912 A1 | 8/2004 | Old et al. | |
| 2004/0167190 A1 | 8/2004 | Stjernschantz et al. | |
| 2004/0171596 A1 | 9/2004 | Prokai et al. | |
| 2004/0180036 A1 | 9/2004 | Ashton et al. | |
| 2005/0222232 A1 | 10/2005 | DeLong et al. | |
| 2006/0121069 A1 | 6/2006 | DeLong et al. | |
| 2006/0135609 A1 | 6/2006 | Toone et al. | |
| 2006/0247214 A1 | 11/2006 | DeLong et al. | |
| 2007/0092466 A1 | 4/2007 | DeLong et al. | |

(Continued)

FOREIGN PATENT DOCUMENTS

DE 235357 5/1911
DE 2942643 5/1981

(Continued)

OTHER PUBLICATIONS

Deshpande et al., J. Ocular Pharmacology, 2000, 46(6), 539-556.*
U.S. Appl. No. 11/174,420, filed Jul. 1, 2005, DeLong et al.
Albert, A., "Chemical aspects of selective toxicity," Nature (1958) 182:421-423.
Ansel, H.C., Introduction to Pharmaceutical Dosage Forms, 2nd edition (1976) Lea & Febiger, Philadelphia.
Artamonov, A.F. et al., "Synthesis of D-mannite esters," Chem. Natural Compounds (2000) 36(4):342-344.
Artamonov, A.F. et al., "Synthesis of the alpha-monoglyceride of trans-O-methyl-marmesic acid and its modified derivatives—the phosphate and citrate," Chem. Natural Compounds (1998) 34(4):423-425.
Audoly, L.P. et al., "Identification of specific EP receptors responsible for the hemodynamic effects of PGE2," Am. J. Physio. (1999) 277(3):H924-30.

(Continued)

Primary Examiner — Kyle Purdy
(74) Attorney, Agent, or Firm — Michael Best & Friedrich LLP

(57) ABSTRACT

The present invention relates generally to ophthamological drugs. More specifically, the invention relates to a method of modifying (derivatizing) ophthamological drugs so as to increase their penetration through the cornea. The invention also relates to drugs modified (derivatized) in accordance with the instant method and to the use of same in treating conditions associated with elevated intraocular pressure, particularly, glaucoma.

25 Claims, 13 Drawing Sheets

(56) References Cited

U.S. PATENT DOCUMENTS

| | | |
|---|---|---|
| 2007/0161699 A1 | 7/2007 | Epstein et al. |
| 2007/0254920 A1 | 11/2007 | DeLong et al. |
| 2008/0103184 A1 | 5/2008 | DeLong et al. |

FOREIGN PATENT DOCUMENTS

| | | |
|---|---|---|
| EP | 0001255 | 4/1979 |
| EP | 0855389 | 7/1998 |
| EP | 1094055 | 4/2001 |
| GB | 1456512 | 11/1976 |
| JP | 0435592 | 10/1992 |
| JP | 11-180949 | 7/1999 |
| WO | WO 93/14743 | 8/1993 |
| WO | WO 95/08990 | 4/1995 |
| WO | WO 95/19165 | 7/1995 |
| WO | WO 98/20880 | 5/1998 |
| WO | WO 99/12895 | 3/1999 |
| WO | WO 99/12896 | 3/1999 |
| WO | WO 99/12898 | 3/1999 |
| WO | WO 99/50241 | 10/1999 |
| WO | WO 99/50242 | 10/1999 |
| WO | WO 00/04898 | 2/2000 |
| WO | WO 00/51980 | 9/2000 |
| WO | WO 01/10873 | 2/2001 |
| WO | WO 01/74307 | 10/2001 |
| WO | WO 01/74313 | 10/2001 |
| WO | WO 01/74314 | 10/2001 |
| WO | WO 01/74315 | 10/2001 |
| WO | WO 02/12549 | 2/2002 |
| WO | WO 00/51979 | 9/2002 |
| WO | WO 2006/047466 | 5/2006 |
| WO | WO 2007/127639 | 11/2007 |

OTHER PUBLICATIONS

Babiole, Maggy, et al., "In Vitro Corneal Permeation of Unoprostone Isopropyl (UI) and its Metabolism in the Isolated Pig Eye," *J. Ocular Pharmacology and Therapeutics*, 2001, p. 159-72, vol. 17, No. 2, Mary Ann Liebert, Inc. Publishers.

Banker, Gilbert S., and Christopher T. Rhodes, ed., *Modern Pharmaceutics*, 1979, chapters 9 and 10, Marcel Dekker, Inc., New York.

Bundy, Gordon L., and F. H. Lincoln, "Synthesis of 17-Phenyl-18,19,20-Trinorprostaglandins," *Prostaglandins*, 1975, p. 1-4, vol. 9, No. 1, Geron-X.

Chyun, Yong S., and Lawrence G. Raisz, "Stimulation of Bone Formation by Prostaglandin $E_2$," *Prostaglandins*, 1984, p. 97-103, vol. 27, No. 1, Geron-X.

Collins, Paul W., and Stevan W. Djuric, "Synthesis of Therapeutically Useful Prostaglandin and Prostacyclin Analogs," *Chemical Reviews*, 1993, p. 1533-64, vol. 93, No. 4, American Chemical Society.

Corey, E. J., et al., Stereo-Controlled Synthesis of Prostaglandins $F_{2\alpha}$ and $E_2$ (dl), *Journal of the American Chemical Society*, 1969, p. 5675-77, vol. 91, No. 20, American Chemical Society.

Corey, E. J., et al., "Total Synthesis of Prostaglandins $F_{2\alpha}$ and $E_2$ as the Naturally Occurring Forms," *J. Am. Chem., Soc.*, 1970, p. 397-98, vol. 92, No. 2, American Chemical Society.

Cynkowska, G. et al., "Synthesis and properties of novel antiglaucoma prodrugs and codrugs of ethacrynic acid," Pharm. Res. (1995) 12(9):S229.

Deshpande, G. et al., "In vitro and ex vivo hydrolysis rates of ethacrynate esters and their relationship to intraocular pressure in the rabbit eye," J. Ocular Pharmacol. Therap. (2000) 16(6):539-556.

Gennaro, Alfonso R., ed., *Remington's Pharmaceutical Sciences*, 18th ed., 1990, Mack Publishing Company, Easton, Pennsylvania.

Goldberg et al., Functional Foods (1994), Springer, Chapter 11, Kauko K. Makinen author, p. 219-220.

Gomis, P., "Preparation et proprietes de quelques esters de la phenoxymethylpenicilline," Bulletin de la Societe Chimique de France (1968) 1:420-424.

Greene, Theodora W. and Peter G. M. Wuts, "Protection for the Hydroxyl Group, Including 1,2- and 1,3-Diols," *Protecting Groups in Organic Synthesis*, 2nd ed., 1991, p. 10-142, John Wiley & Sons, Inc., New York.

Hallinan, E. Ann, et al., "Aminoacetyl Moiety as a Potential Surrogate for Diacylhydrazine Group of SC-51089, a Potent $PGE_2$ Antagonist, and Its Analogs," *Journal of Medicinal Chemistry*, 1996, p. 609-13, vol. 39, No. 2, American Chemical Society.

Hartke, J. R., et al., "Prostanoid FP Agonists Build Bone in the Ovariectomized Rat," *Journal of Bone and Mineral Research*, 1999, p. S207, vol. 14, abstract T326, 1999 Program & Abstracts, Blackwell Science, Inc.

Iguchi, Y., et al., "Synthesis of Prostaglandins Containing the Sulfo Group," *J. Org. Chem.*, vol. 40, No. 4, 1975, p. 521-23, American Chemical Society.

Kerstetter, J. R., et al., "Prostaglandin $F_{2\alpha}$-1-Isopropylester Lowers Intraocular Pressure Without Decreasing Aqueous Humor Flow," *American Journal of Ophthalmology*, series 3, 1988, p. 30-34, vol. 105, No. 1, Ophthalmic Publishing Company.

Kiriyama, Michitaka, et al., "Ligand binding specificities of the eight types and subtypes of the mouse prostanoid receptors expressed in Chinese hamster ovary cells," *British Journal of Pharmacology*, 1997, p. 217-224, vol. 122, Stockton Press.

Kluender, Harold C., and Warren Woessner, "The Synthesis of Dimethylphosphonoprostaglandin Analogs," *Prostaglandins and Medicine*, 1979, p. 441-44, vol. 2, No. 6, Churchill Livingstone.

Kozak, F., "Metabolism of prostaglandin glycerol esters and prostaglandin ethanolamides in vitro and in vivo," J. Biol. Chem. (2001) 276(4):36993-36998.

Lieberman, Herbert A., et al., ed., *Pharmaceutical Dosage Forms: Tablets*, 2nd ed., 1990, Marcel Dekker, Inc., New York.

Liljebris, C. et al., "Derivatives of 17-phenyl-18, 19, 20 trinorprostaglan F2alpha isopropyl ester: potential antiglaucoma agents," J. Med. Chem. (1995) 38(2):289-304.

Lundy, M. W., et al., "Restoration of Cancellous Architecture and Increased Bone Strength in Aged Osteopenic Rats Treated with Fluprostenol," *Journal of Bone and Mineral Research*, 1999, p. S401, vol. 14, abstract S368, 1999 Program & Abstracts, Blackwell Science, Inc.

Ma, M. et al., "HPLC and LC-MS studies of the transesterification reaction of methylparaben with twelve 3- to 6-carbon sugar alcohols and propylene glycol and the isomerization of the reaction products by acyl migration," J. Chrom. Sci. (2002) 40:170-177.

Marcason, "What do 'net carb,' 'low carb' and 'impact carb' really mean on food labels," J. Amer. Dietetic Assoc. (2004) 104(1):135.

Matsumura, H., "Prostaglandins and Sleep," *Saishin No to Shinkei Kagaku Shirizu*, 1998, 10, 79-89.

McCutcheons's 1994, North American Edition, (Emulsifiers & Detergents), MC Publishing Company, Glen Rock, New Jersey (1994) 1:236-239.

Mori, S., et al., "Effects of Prostaglandin $E_2$ on Production of New Cancellous Bone in the Axial Skeleton of Ovariectomized Rats," *Bone*, 1990, p. 103-13, vol. 11, No. 2, Pergamon Press, New York.

MSDS, propanoic acid, http://www.jtbaker.com/msds/englishhtml/p6643.htm.

Narumiya, Shuh, "Roles of prostanoids in health and disease; lessons from receptor-knockout mice," *Common Disease: Genetic and Pathogenetic Aspects of Multifactorial Diseases*, 1999, p. 261-69, Elsevier Science B.V.

Negishi, Manabu, et al., "Molecular mechanisms of diverse actions of prostanoid receptors," *Biochimica et Biophysica Acta*, 1995, p. 109-19, vol. 1259, No. 1, Elsevier Science B.V.

Ohno, M. et al., "Chiral synthons by ester hydrolysis catalyzed by pig liver esterase," Org. Reactions (1989) 37:1-55.

Roche, Edward B., ed., *Design of Biopharmaceutical Properties Through Prodrugs and Analogs*, 1997, American Pharmaceutical Association Academy of Pharmaceutical Sciences, Washington, D.C.

Roof, S. L., et al., "mRNA Expression of Prostaglandin Receptors $EP_1$, $EP_2$, $EP_3$, and $EP_4$ in Human Osteoblast-Like Cells and 23 Human Tissues," *Journal of Bone and Mineral Research*, 1996, p. S174, vol. 11, abstract S337, 1996 Program & Abstracts, Blackwell Science, Inc.

Ruel, Réjean, et al., "New Class of Biphenylene Dibenzazocinones as Potent Ligands for the Human $EP_1$ Prostanoid Receptor," *Bioorganic & Medicinal Chemistry Letters*, 1999, p. 2699-2704, vol. 9, Elsevier Science Ltd.

(56) References Cited

OTHER PUBLICATIONS

Sakuma, Yoko, et al., "Crucial Involvement of the EP4 Subtype of Prostaglandin E Receptor in Osteoclast Formation by Proinflammatory Cytokines and Lipopolysaccharide," *Journal of Bone and Mineral Research*, 2000, p. 218-27, vol. 15, No. 2, American Society for Bone and Mineral Research.

Shih, Mei-Shu and Robert W. Norrdin, "$PGE_2$ induces regional remodeling changes in haversian envelope: a histomorphometric study of fractured ribs in Beagles," 1986, p. 227-34, *Bone and Mineral*, vol. 1, Elsevier Science Publishers B.V.

Shimazaki, A., et al. "New Ethacrynic Acid Derivatives as Potent Cytoskeletal Modulators in Trabecular Meshwork Cells," Biol. Pharm. Bull. vol. 27, No. 6, 2004, pp. 846-850.

Shimazaki, A., et al., "Effects of the New Ethacrynic Acid Derivative SA9000 on Intraocular Pressure in Cats and Monkeys," Biol Pharm. Bull. vol. 27, No. 7, 2004, pp. 1019-1024.

Tamm, C. et al., "Pig liver esterase catalyzed hydrolysis: substrate specificity and steroselectivity," Pure and Applied Chemimstry (1992) 64(8):1187-1191.

Wenninger, John A., and G. N. McEwen, Jr., ed., *CTFA Cosmetic Ingredient Handbook*, 2$^{nd}$ ed., 1992, p. 587-92, The Cosmetic, Toiletry, and Fragrance Association, Washington, D.C.

Willis, Anthony L., *Handbook of Eicosanoids: Prostaglandins and Related Lipids*, vol. I, Part A, CRC Press, Inc., Boca Raton, Florida, 1987.

Willis, Anthony L., *Handbook of Eicosanoids: Prostaglandins and Related Lipids*, vol. I, Part B, CRC Press, Inc., Boca Raton, Florida, 1987.

Zlatkov, A., "Synthesis, toxicology, pharmacological assessment, and in vitro bronchodilating activity of some 7-theophyllinylacetyloxyglycols," Arch. Pharm. Pharm. Med. Chem. (1998) 331(10):313-318.

United States Patent Office Action for U.S. Appl. No. 11/255,478 dated Jan. 29, 2009 (14 pages).

United States Patent Office Action for U.S. Appl. No. 11/255,478 dated May 14, 2008 (11 pages).

United States Patent Office Action for U.S. Appl. No. 11/255,478 dated Oct. 15, 2007 (12 pages).

United States Patent Office Action for U.S. Appl. No. 11/412,207 dated Oct. 23, 2009 (11 pages).

International Search Report and Written Opinion for Application No. PCT/US2005/038287 dated Jun. 7, 2006 (12 pages).

International Search Report and Written Opinion for Application No. PCT/US2007/066782 dated Apr. 24, 2008 (17 pages).

\* cited by examiner

5-O-Ribitol [2,3-dichloro-4-(thiophene-2-carbonyl)]phenoxyacetate

| time | 10% IOP reduction from baseline, mmHg | | 15% IOP reduction from baseline, mmHg | |
|---|---|---|---|---|
| | control (n= 4) | ticrynafen (n= 4) | control (n= 4) | ticrynafen (n= 4) |
| baseline | 23.6 | 23.4 | 21.9 | 22.2 |
| 24 hrs | 21.1 (-2.3) | 20.6 (-2.8) | 22.8 (+0.9) | 23.2 (+1.0) |
| 48 hrs | 22.4 (-1.2) | 21.0 (-2.4) | 21.8 (-0.1) | 21.0 (-1.2) |
| 72 hrs | 20.3 (-3.3) | 19.9 (-3.5) | 20.3 (-1.6) | 20.6 (-1.6) |
| 6 days | 22.2 (-1.4) | 22.0 (-1.6) | 24.3 (+2.4) | 23.7 (+1.5) |

| time | | 0.3% IOP (Change from Baseline), mmHg | | IOP Change from Untreated Control, mmHg | 0.6% IOP (Change from Baseline), mmHg | | IOP Change from Untreated Control, mmHg |
|---|---|---|---|---|---|---|---|
| | | untreated (n=7) | treated (n=7) | | untreated (n=7) | treated (n=7) | |
| Day 1 | morning | 21.2±0.5 (0) | 21.0±0.6 (0) | -0.2 | 18.6±1.1 (0) | 18.5±1.0 (0) | -0.1 |
| | afternoon | 20.7±0.7 (-0.5) | 19.2±0.7 (-1.8) | -1.5 | 19.5±1.4 (+0.9) | 17.9±1.2 (-0.6) | -1.6 |
| Day 2 | morning | 20.6±0.5 (-0.6) | 19.1±0.6 (-1.9) | -1.5 | 19.4±1.2 (+0.8) | 17.7±1.1 (-0.8) | -1.7 |
| | afternoon | 21.7±0.6 (+0.5) | 19.5±0.7 (-1.5) | -2.2 | 20.1±0.9 (+1.5) | 18.0±0.9 (-0.5) | -2.1 |
| Day 3 | morning | 20.6±0.7 (-0.6) | 18.9±0.6 (-2.1) | -1.7 | 19.5±0.9 (+0.9) | 17.3±1.1 (-1.2) | -2.2 |
| | afternoon | 20.8±0.7 (-0.3) | 19.0±0.7 (-2.0) | -1.8 | 19.7±1.4 (+1.1) | 17.9±1.3 (-0.6) | -1.8 |
| Day 4 | morning | 21.1±0.4 (-0.1) | 19.2±0.4 (-1.8) | -1.9 | 19.3±1.3 (+0.7) | 17.3±1.2 (-1.2) | -2.0 |
| | afternoon | 20.0±0.6 (-1.2) | 18.1±0.7 (-2.9) | -1.9 | 19.4±1.3 (+0.8) | 17.5±1.2 (-1.0) | -1.9 |
| Day 5 | morning | 21.0±0.6 (-0.2) | 19.1±0.9 (-1.9) | -1.9 | 19.6±1.1 (+1.0) | 17.6±1.0 (-0.9) | -2.0 |
| | afternoon | 21.8±0.6 (+0.6) | 19.4±0.8 (-1.6) | -2.4 | 20.2±1.6 (+1.6) | 18.0±1.5 (-0.5) | -2.2 |
| Day 6 | morning | 20.9±0.8 (-0.2) | 19.0±0.9 (-2.0) | -1.9 | 20.2±1.3 (+1.6) | 18.2±1.1 (-0.3) | -2.0 |
| | afternoon | 21.5±0.9 (+0.3) | 19.1±1.0 (-1.9) | -2.4 | 20.1±1.4 (+1.5) | 18.3±1.5 (-0.2) | -1.8 |
| Day 7 | morning | 21.0±0.4 (-0.2) | 19.2±0.7 (-1.8) | -1.8 | 20.7±0.8 (+2.1) | 18.3±0.9 (-0.2) | -2.4 |
| | afternoon | 21.8±0.5 (+0.6) | 19.6±0.8 (-1.4) | -2.2 | 20.7±0.8 (+2.1) | 18.5±1.2 (0) | -2.2 |

FIG. 7 (cont'd)

5-O-{(9α,11α,15R)-15-[2-Benzo[b]thiophen-2-yl]-16,17,18,19,20-pentanor-5,6,13,14-tetrahydro-9,11,15-trihydroxyprostanoyl}xylitol

| time | | 0.004% IOP (Change from Baseline), mmHg | | IOP Change from Untreated Control, mmHg | 0.02% IOP (Change from Baseline), mmHg | | IOP Change from Untreated Control, mmHg |
|---|---|---|---|---|---|---|---|
| | | untreated (n=4) | treated (n=4) | | untreated (n=4) | treated (n=4) | |
| Day 1 | morning | 24.0±0.8 (0) | 24.0±0.9 (0) | 0 | 18.1±1.2 (0) | 17.5±1.8 (0) | -0.6 |
| | afternoon | 25.1±0.5 (+1.1) | 22.3±0.4 (-1.7) | -2.8 | 17.3±1.2 (-0.8) | 14.5±1.3 (-3.0) | -2.8 |
| Day 2 | morning | 25.5±0.7 (+1.5) | 23.3±0.6 (-0.7) | -2.2 | 18.0±0.9 (-0.1) | 16.5±0.7 (-1.0) | -1.5 |
| | afternoon | 24.1±0.9 (+0.1) | 22.4±0.7 (-1.6) | -1.7 | 17.6±1.2 (-0.5) | 15.2±1.3 (-2.3) | -2.4 |
| Day 3 | morning | 24.2±0.7 (+0.2) | 22.8±0.8 (-1.2) | -1.4 | 17.6±1.4 (-0.5) | 15.8±1.0 (-1.7) | -1.8 |
| | afternoon | 25.1±0.7 (+1.1) | 23.5±0.6 (-0.5) | -1.6 | 17.6±1.2 (-0.5) | 15.3±1.3 (-2.2) | -2.3 |
| Day 4 | morning | 24.0±1.2 (0) | 22.0±0.9 (-2.0) | -2.0 | 17.2±0.9 (-0.9) | 15.8±1.0 (-1.7) | -1.4 |
| | afternoon | 23.2±0.4 (-0.8) | 22.0±0.3 (-2.0) | -1.2 | 19.8±1.1 (+1.7) | 16.8±0.9 (-0.7) | -3.0 |
| Day 5 | morning | 23.3±0.6 (-0.7) | 22.1±0.7 (-1.9) | -1.2 | 18.5±1.1 (+0.4) | 16.5±0.9 (-1.0) | -2.0 |
| | afternoon | 24.9±0.7 (+0.9) | 23.0±0.3 (-1.0) | -1.9 | 17.8±0.8 (-0.3) | 15.9±0.9 (-1.6) | -1.9 |

FIG. 9 (cont'd)

11-Hydroxy-3,6,9-trioxaundecyl 4-(2-phenylacryloyl)cinnamate

| | 0.3% | | IOP Change from Untreated Control, mmHg | 0.6% | | IOP Change from Untreated Control, mmHg |
|---|---|---|---|---|---|---|
| | IOP (Change from Baseline), mmHg | | | IOP (Change from Baseline), mmHg | | |
| time | untreated (n=4) | treated (n=4) | | untreated (n=4) | treated (n=4) | |
| Day 1 morning | 22.8±0.2 (0) | 22.7±0.6 (0) | -0.1 | 24.1±0.6 (0) | 24.1±0.6 (0) | 0 |
| afternoon | 22.5±0.5 (-0.3) | 21.3±0.5 (-1.4) | -1.2 | 23.6±0.4 (-0.5) | 22.5±0.5 (-1.6) | -1.1 |
| Day 2 morning | 22.8±0.3 (0) | 21.1±0.6 (-1.6) | -1.7 | 23.7±0.7 (-0.4) | 22.5±0.9 (-1.6) | -1.2 |
| afternoon | 23.5±0.3 (+0.7) | 22.2±0.4 (-0.5) | -1.3 | 24.6±0.8 (+0.5) | 23.0±0.7 (-1.1) | -1.6 |
| Day 3 morning | 23.5±1.0 (+0.7) | 22.6±0.4 (-0.1) | -0.9 | 23.5±0.9 (-0.6) | 22.0±1.0 (-2.1) | -1.5 |
| afternoon | 23.0±0.8 (+0.2) | 22.4±0.6 (-0.3) | -0.6 | 24.5±1.2 (+0.4) | 22.9±1.0 (-1.2) | -1.6 |
| Day 4 morning | 23.8±0.9 (+1.0) | 22.3±1.0 (-0.4) | -1.5 | 24.1±0.5 (0) | 22.3±0.6 (-1.8) | -1.8 |
| afternoon | 23.8±0.5 (+1.0) | 22.5±0.6 (-0.2) | -1.3 | 25.2±1.2 (+1.2) | 23.3±0.8 (-0.8) | -1.9 |
| Day 5 morning | 22.9±0.6 (+0.1) | 22.3±0.9 (-0.4) | -0.6 | 23.3±0.7 (-0.8) | 21.3±0.6 (-2.8) | -2.0 |
| afternoon | 21.3±0.6 (-1.5) | 20.8±0.8 (-1.9) | -0.5 | 23.3±0.3 (-0.8) | 22.1±0.5 (-2.0) | -1.2 |
| Day 6 morning | 22.3±0.9 (-0.5) | 21.2±1.0 (-1.5) | -1.1 | 23.9±1.0 (-0.2) | 22.4±0.6 (-1.7) | -1.5 |
| afternoon | 22.7±0.6 (-0.1) | 21.6±0.8 (-1.1) | -1.1 | 23.8±0.6 (-0.3) | 22.3±0.5 (-1.8) | -1.5 |
| Day 7 morning | 22.3±0.9 (-0.5) | 21.0±0.9 (-1.7) | -1.3 | 24.4±0.8 (+0.3) | 22.9±0.7 (-1.2) | -1.5 |
| afternoon | 23.6±0.1 (+0.8) | 22.0±0.7 (-0.7) | -1.6 | 23.8±1.0 (-0.3) | 22.3±0.6 (-1.8) | -1.5 |

FIG. 10 (cont'd)

OPHTHAMOLOGICAL DRUGS

CROSS-REFERENCE TO RELATED APPLICATIONS

This application is a divisional of U.S. patent application Ser. No. 11/255,478, filed Oct. 21, 2005, which claims priority to U.S. Provisional Patent Application No. 60/620,320 filed Oct. 21, 2004, both of which are incorporated herein by reference in their entirety.

TECHNICAL FIELD

The present invention relates, in general, to ophthamological drugs, and, in particular, to a method of modifying ophthamological drugs so as to increase their penetration through the cornea into the anterior chamber. The invention further relates to such modified drugs and to the use of same in treating diseases/disorders of the eye, such as glaucoma and other conditions related to elevated intraocular pressure.

BACKGROUND

Glaucoma is one of the three leading causes of blindness in the United States and a leading cause of blindness in the world. Over 2.2 million people in the United States have glaucoma, and several million more are at risk of developing the disease. As the population ages, the number of individuals with glaucoma will continue to grow since glaucoma affects the oldest individuals disproportionately.

Glaucoma is not just one disease, rather, it is a spectrum of conditions that share a final common pathway of acquired, progressive deterioration of the neuronal components of the optic nerve. The neuronal death results in loss of vision once a sufficient number of individual nerves are destroyed.

Factors associated with the development of glaucoma and its progression have been identified and are in the process of being clarified. Elevated intraocular pressure (IOP) is the leading cause of glaucoma. Pressure is elevated because drainage of aqueous fluid from within the eye is impaired.

Current treatments for glaucoma center on reducing pressure in the eye by reducing the amount of aqueous fluid being produced or by enhancing the flow of fluid out of the eye by mechanical or other means. Topical agents that are presently in use include miotics, which increase the outflow of fluid (these include Isopto®Carpine, Ocusert®, Pilocar®, and Pilopine®); epinephrines, which also increase the outflow of fluid (these include Epifrin® and Propine®); beta-blockers, which reduce the amount of fluid (these include Betagan®, Betimol®, Betoptic®, Ocupress®, Optipranalol®, and Timoptic®); and carbonic anhydrase inhibitors and alpha-adrenergic agonists, which also reduce the amount of fluid (these include Alphagan®, Iopidine®, and Trusopt®). Prostaglandin analogs, which are also in use, increase the outflow of fluid through a secondary drainage route (these include Lumigan®, Rescula®, Travatan®, and Xalatan®). (Common oral medications include carbonic anhydrase inhibitors (such as Daranide®, Diamox®, and Neptazane®). These agents decrease aqueous humor inflow into the eye.)

Glaucoma patients may also suffer reduced blood flow to the optic nerve and neuronal tissue, and diminished resistance of the nerve tissue to damage, and the compliance of connective tissue surrounding and supporting the optic nerve. One agent, Memantine, is in phase III clinical trials (Allergan) as an agent that may prove to be neuroprotective.

The topical application of ophthamological drugs for the treatment of glaucoma requires penetration of the drug through the cornea and into the anterior chamber, which contains aqueous humor, which then drains into the conventional outflow pathway (trabecular meshwork and Schlemm's canal) and the uveal-scleral pathway (unconventional outflow pathway). Intraocular pressure is lowered by drugs acting in the trabecular meshwork/Schlemm's canal and the uveal-scleral pathway. Penetration of the drug through the cornea requires a balance of hydrophobic and hydrophilic characteristics. The drug must be sufficiently soluble in non-polar media to diffuse into the cornea and sufficiently soluble in polar (aqueous) media to diffuse out of the cornea into the aqueous humor.

Many drugs potentially useful for the treatment of glaucoma are carboxylic acids (e.g., phenoxyacetic acids or cinnaminic acids). Carboxylic acids are typically delivered in buffered aqueous solution; near neutral pH, carboxylic acids exist as the deprotonated carboxylate salt. Ionized carboxylate salts, while soluble in aqueous solution, will not penetrate the cornea. Such drugs can be delivered as pro-drug esters. The use of pro-drug esters, which are cleaved enzymatically (e.g., in the cornea) to regenerate the active compound, can enhance penetration of drug through the cornea into the anterior chamber.

Unfortunately, many esters are too hydrophobic (non-polar) to diffuse out of the relatively non-polar external layer of the cornea (corneal epithelium) and into the aqueous humor. Further complicating delivery, such compounds are often too insoluble to formulate in aqueous solutions.

The present invention provides a method of preparing derivatives of ophthalmological drugs that contain a carboxyl group so as to overcome solubility and corneal penetration limitations associated with such drugs. The present approach results in the production of pro-drugs that can diffuse into the cornea of mammalian eyes but that are sufficiently water soluble to be released from the cornea into the aqueous humor. Pro-drugs of the invention are activated by esterases in the cornea, with the result that the active drug is present in the aqueous humor of the anterior chamber.

SUMMARY OF THE INVENTION

The present invention relates generally to ophthamological drugs. More specifically, the invention relates to a method of modifying (derivatizing) ophthamological drugs so as to increase their penetration through the cornea. The invention also relates to drugs modified (derivatized) in accordance with the instant method and to the use of same in treating conditions associated with elevated intraocular pressure, particularly, glaucoma.

In one embodiment, the invention provides a composition comprising a compound derived from the esterification of a carboxylate functionality of a drug moiety with a sugar alcohol, the drug moiety comprising at least one of a phenoxyacetic acid, a cinnamic acid, and a mixture thereof.

In another embodiment, the invention provides a composition comprising a compound derived from the esterification of a carboxylate functionality of a drug moiety thereof, with the proviso that the drug moiety is not a prostaglandin.

In yet another embodiment, the invention provides a compound selected from the group consisting of:
5-O-Ribitol [2,3-dichloro-4-(thiophene-2-carbonyl)]phenoxyacetate;
5-O-Xylitol 4-(2-phenylacryloyl)cinnamate;
5-O-{(9α,11α,15R)-15-[2-Benzo[b]thiophen-2-yl]-16,17,18,19,20-pentanor-5,6,13,14-tetrahydro-9,11,15-trihydroxyprostanoyl}xylitol;

11-Hydroxy-3,6,9-trioxaundecyl 4-(2-phenylacryloyl)cinnamate;
5-O-{(9α,11α,15R)-15-[2-Benzo[b]thiophen-2-yl]-16,17,18,19,20-pentanor-5,6,13,14-tetrahydro-9,11,15-trihydroxyprostanoyl}xylitol;
5-O-{(9α,11α,15R)-15-[2-Benzo[b]thiophen-2-yl]-16,17,18,19,20-pentanor-5,6,13,14-tetrahydro-9,11,15-trihydroxyprostanoyl}-D-ribitol;
4-O-{(9α,11α,15R)-15-[2-benzo[b]thiophen-2-yl]-16,17,18,19,20-pentanor-5,6,13,14-tetrahydro-9,11,15-trihydroxyprostanoyl}-L-threitol;
5-O-Xylitol 4-(2-phenylacryloyl)cinnamate;
1-O-D-Sorbitol 4-(2-phenylacryloyl)cinnamate;
1-O-D-Arabitol 4-(2-phenylacryloyl)cinnamate;
1-O-Glycerol [2,3-dichloro-4-(2-methylenebutyryl)]phenoxyacetate;
1-O-Erythritol [2,3-dichloro-4-(2-methylenebutyryl)]phenoxyacetate;
1-O-Ribitol [2,3-dichloro-4-(2-methylenebutyryl)]phenoxyacetate;
5-O-Ribitol [2,3-dichloro-4-(thiophene-2-carbonyl)]phenoxyacetate;
2-O-D-Sorbitol 4-(2-phenylacryloyl)cinnamate; and
2-O-Ribitol [2,3-dichloro-4-(2-methylenebutyryl)]phenoxyacetate.

In a further embodiment, the invention provides a method of treating an ophthamological disorder, said method comprising administering to a human or other animal a safe and effective amount of a compound derived from the esterification of a carboxylate functionality of a drug moiety with a sugar alcohol, the drug moiety comprising at least one of a phenoxyacetic acid, a cinnamic acid, and a mixture thereof.

In another embodiment, the invention provides a method of determining the suitability of a compound for treating an ophthamological disorder, said method comprising providing a compound derived from the esterification of a carboxylate functionality of a drug moiety with a sugar alcohol, determining whether the compound releases its carboxcylic acid, in an assay under conditions mimicking conditions in an eye, within a predetermined half life, and selecting the compound for treatment of an ophthamological disorder if the compound releases its carboxcylic acid within the predetermined half life.

In yet another embodiment, the invention provides a compound derived from the esterification of a carboxylate functionality of a drug moiety with a sugar alcohol, the drug moiety being at least one of travaprost, latanoprost, and bimatoprost and mixtures thereof.

Objects and advantages of the present invention will be clear from the description that follows. All references or other sources of information cited herein are incorporated herein by reference.

DETAILED DESCRIPTION OF THE INVENTION

Terms and Definitions

Figure 1:
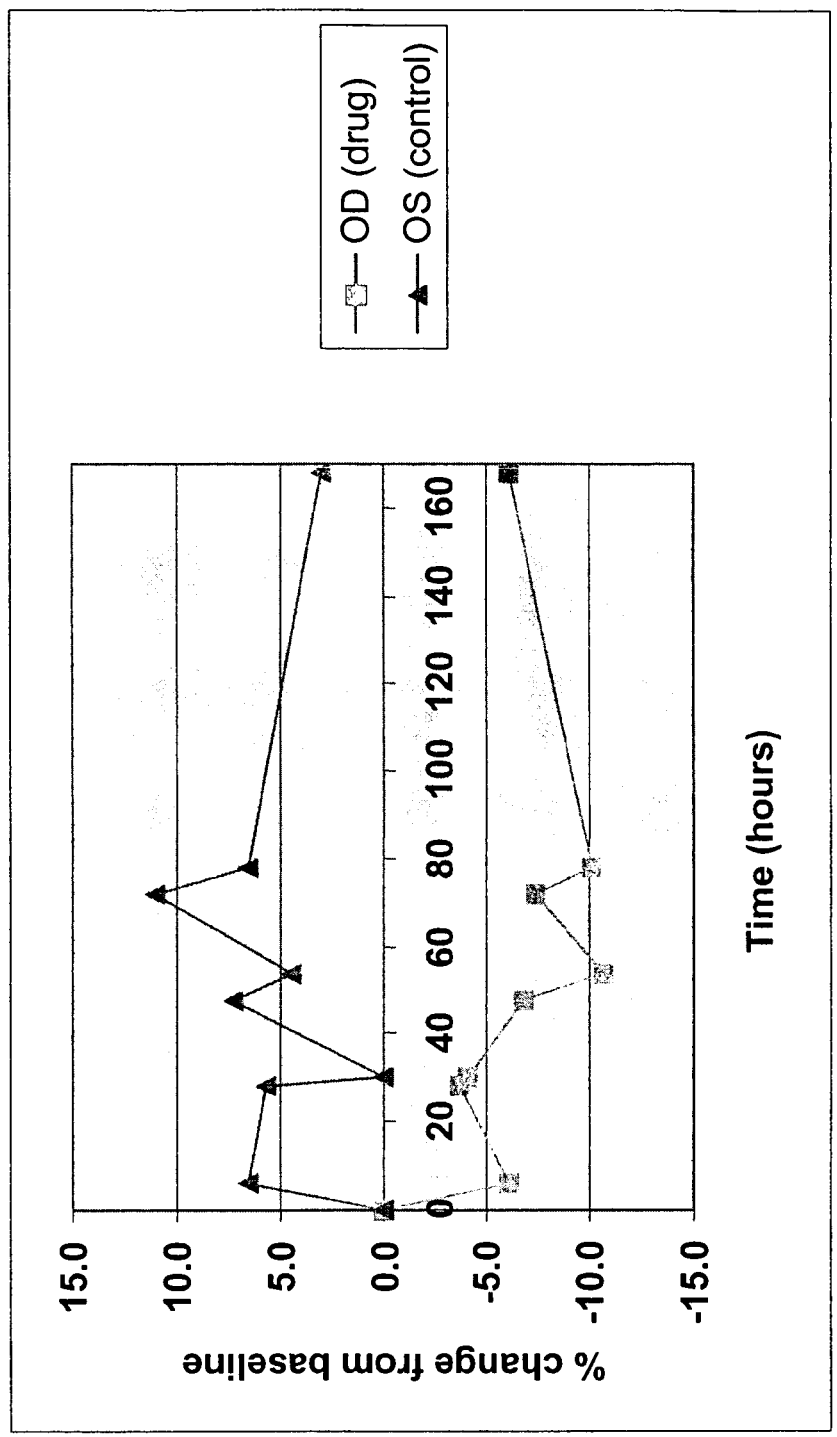
FIG. 1. Pressure reduction observed with 5% formulation of ticrynafen-ribotol ester.

As used herein, "alkyl" refers to a saturated or unsaturated hydrocarbon chain having 1 to 12 carbon atoms, preferably 1 to 6, more preferably 1 to 3 carbon atoms. Alkyl chains may be straight or branched. Preferred branched alkyl moieties have one or two branches, preferably one branch. Preferred alkyl moieties are saturated. Unsaturated alkyl moieties have one or more double bonds and/or one or more triple bonds. Preferred unsaturated alkyl moieties have one or two double bonds or one triple bond, more preferably one double bond. Alkyl chains may be unsubstituted or substituted with from 1 to 4 substituents. Preferred substituted alkyl moieties are mono-, di-, or trisubstituted. The substituents may be lower alkyl, halo, hydroxy, aryloxy, acyloxy (e.g., acetoxy), carboxy, monocyclic aromatic ring (e.g., phenyl), monocyclic heteroaromatic ring, monocyclic carbocyclic aliphatic ring, monocyclic heterocyclic aliphatic ring, and amino moieties.

As used herein, "carboxylate" and "carboxylic acid" refer to a chemical moiety characterized by a carbon atom attached to three substituents, viz., another carbon atom by a single bond, an oxygen atom by a double bond, and another oxygen atom by a single bond. The shorthand "XCOO—" and "X—COOH" as used herein shall constitute shorthand for the carboxylate and the carboxylic acid moieties, respectively. In this shorthand "X" shall indicate the rest of the drug moiety that contains the carboxylic acid. It is understood that "X" must contain a carbon atom directly attached to the carboxylic acid moiety.

As used herein, "opthamological drugs" refers to any chemical compound that is applied to the eye with the intent of producing a biological response or to treat a disease or condition of the eye. Non-limiting examples of opthamological drugs include the prostaglandins, such as travaprost, latanoprost, bimatoprost and similar agents, phenoxyacetic acids, cinnamic and phenylproprionic acids, benzoic acids, fatty acids, and the like. Conditions and diseases include but are not limited to glaucoma and macular degeneration.

As used herein, "sugar alcohol" refers to an alcohol that contains multiple hydroxyl groups along a carbon chain. "Sugar alcohols" may be naturally occurring, or may be derived from a naturally-occurring sugar or a different sugar alcohol, or may be partially or wholly derived from a synthetic pathway. "Sugar alcohols" may have no more than one hydroxyl per carbon atom of the chain, but they may have less than a 1:1 ratio. "Sugar alcohols" must have at least one free hydroxyl besides the one that is used to create the ester linkage. The carbon chain of the sugar alcohol may have up to 9 carbon atoms, and may be entirely linear, or may be branched, or may contain rings. Other atoms or groups of atoms may independently replace each of the hydroxyl groups as long as there is at least one free hydroxyl group remaining. Non-limiting examples of suitable replacement moieties include alkyl groups, chlorine atoms, methoxy groups, phenoxy groups alkoxy groups, fluorine atoms, amine groups that may be unsubstituted or mono- or di-substituted, amide groups wherein the amide is attached to the sugar alcohol via the carbon or the nitrogen of the amide. When not free, the hydroxyl groups of the sugar alcohol may be linked together via ketal linkages.

Compounds

The present invention relates to a method of preparing derivatives of ophthamological drugs that comprise a carboxyl group, including drugs suitable for use in treating glaucoma and other diseases/disorders that are associated with elevated intraocular pressure. The present approach results in the production of compounds that can diffuse into the cornea of the mammalian (e.g., human) eye. According to current concepts, enzymatic activation occurs via esterases present in the cornea, resulting in the production of free acid in the anterior chamber/aqueous humor which can then enter the trabecular meshwork/Schlemm's canal or uveal-scleral pathway.

It has been surprisingly found that the disadvantages of current ocular therapy with compounds containing a carboxylic acid can be overcome by a very specific modification. The attachment to the carboxylate group of a sugar alcohol by means of an ester linkage creates a molecule that has improved aqueous solubility over simple esters, better corneal penetration than free carboxylates, and yet at the same time being subject to hydrolysis in vivo at a rate that ensures effective treatment of the underlying condition, particularly glaucoma. This solution is general, not being limited to one type of carboxylate, and the suitability of a carboxylate for this type of modification is easily determined by testing the sugar alcohol ester with commercially-available esterase in vitro, without the need for expensive in vivo testing.

In accordance with the present invention, the carboxylate functionality of the drug is masked (protected) by esterification with a sugar alcohol. Such esterification renders the drug sufficiently hydrophobic to permit diffusion into the cornea. The polar alcohol moiety imparts sufficient aqueous solubility that release from the cornea of active drug into the aqueous humor is effected.

Non-Limiting Examples and Formulae representing the invention are shown below. Where no stereochemistry is shown, it is to be understood that both the R and the S isomeric forms at each stereocenter are all independently individually and specifically contemplated.

The invention includes compounds of formulas IA-C.

   Formula IA wherein:

(X—COO) is the drug moiety; and

SA is a sugar alcohol, attached to either a primary, secondary, or tertiary hydroxyl, the sugar alcohol containing more than 3 but fewer than 9 carbons, and having a ratio of hydroxyl groups to carbons of less than 1:1, but containing at least one free hydroxyl wherein any missing hydroxyl groups are independently replaced by the following a chlorine atom, an amine group, an amido group, an amide group, a fluorine atom, a hydrogen atom, a nitrile group, an aryloxy group and any missing hydrogen groups are replaced by alkyl groups.

   Formula IB wherein:

(X—COO) is the drug moiety;

Y is independently selected from H, OH or OR;

R is $(CH_2)_n CH_3$;

m is 1 to 6 (preferably, m is 1, 2, 3 or 4); and n is 0 to 6 (preferably, n is 0-4).

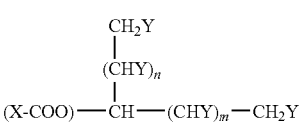   Formula IC wherein:

(X—COO) is the drug moiety;

each Y is independently H, OH, or OR;

R is an alkyl group;

m and n are each independently 0 to 6; and the sum of m+n is less than 9.

Where appropriate, compounds of Formulas IA-C can be present as a pharmaceutically acceptable salt. Suitable salts can be formed with pharmaceutically acceptable anions (e.g., halides, acetate, benzoate, etc.) and cations (e.g., alkali metals, alkali earth metals, alkyl ammonium, etc.).

Compounds of the present invention can be prepared using standard techniques (see, for instance, Examples 1 and 4).

Non-limiting examples of drug moiety that can be derivatized in accordance with the present invention include phenoxyacetic acids, such as ethacrynic acid and ticrynafen, cinnaminic acids, such as SA9000 and SA8248 (Santen) (Shimazaki et al, Biol. Pharm. Bull. 27:1091-1024 (2004), Shimazaki et al, Biol. Pharm. Bull. 27:846-850 (2004)) and prostaglandin derivatives, including the derivative shown in Formula II below. By way of further example, it is noted that certain presently available drugs, such as Lumigan, Travatan and Xalatan, which are isopropyl esters, can be redesigned so as to be esters of sugar alcohols, as described herein.

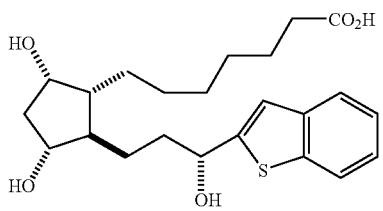

Formula II

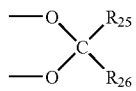

Non-limiting examples of drug moieties can include: Non-steroidal anti-inflammatory agents, such as Acetylsalicylic acid (aspirin), Salicylic acid, Sulindac, Indomethacin, Naproxen, Fenoprofen, Ibuprofen, Ketoprofen, Indoprofen, Furobufen, Diflunisal, Tolmetin, Flurbiprofen, Diclofenac, Mefenamic acid, Flufenamic acid, Meclofenamic acid, Fenclozic acid, Alclofenac, Bucloxic acid, Suprofen, Fluprofen, Cinchophen, Pirprofen, Oxoprozin, Cinmetacin, Acemetacin, Ketorolac, Clometacin, Ibufenac, Tolfenamic acid, Fenclofenac, Prodolic acid, Clonixin, Flutiazin, Flufenisal, Salicylsalicylic acid, O-(Carbamoylphenoxy)acetic acid, Zomepirac, Nifluminic acid, Lonazolac, Fenbufen, Carprofen, Tiaprofenic acid, Loxoprofen, Etodolac, Alminoprofen, 2-(8-Methyl-10,11-dihydro-11-oxodibenz[b,f]oxepin-2-yl)-propionic acid, and 4-Biphenylacetic acid; Cephalosporin antibiotics, such as Cephalothin, Cephacetrile, Cephapirin, Cephaloridine, Cefazolin, Cefazuflur, Ceforanide, Cefazedone, Ceftezole, Cephanone, Cefotiam, Cefamandole, Cefonicid, Cefuroxime, Cefoperazone, Cefpiramide, Cefpimizole, Cefsulodin, Cefoxitin, Cefinetazole, Cefotetan, Cefbuperazone, Cefotaxime, Cefinenoxime, Ceftizoxime, Cefpirome, Ceftazidime, Cefodizime, Ceftriaxone, Latamoxef, Cephalexin, Cephradine, Cefaclor, Cefadroxil, Cefatrizine, Cefroxadine, and Cephaloglycin; Penicillin antibiotics, such as Benzylpenicillin, Phenoxymethylpenicillin, Phenethicillin, Methicillin, Nafcillin, Oxacillin, Cloxacillin, Dicloxacillin, Flucloxacillin, Azidocillin; Ampicillin, Amoxycillin, Epicillin, Cyclacillin, Carbenicillin, Ticarcillin, Sulbenicillin, Azlocillin, Mezlocillin, piperazillin, Apalcillin, Temocillin, Carfecillin, Carindacillin, and Hetacillin; 4-Quinolone antibiotics, such as Ciprofloxacin, Norfloxacin, Acrosoxacin, Pipemidic acid, Nalidixic acid, Enoxacin, Ofloxacin, Oxolinic acid, Flumequine, Cinoxacin, Piromidic acid and Pefloxacin; Steroidal monocarbxylic acids having the following structural formula

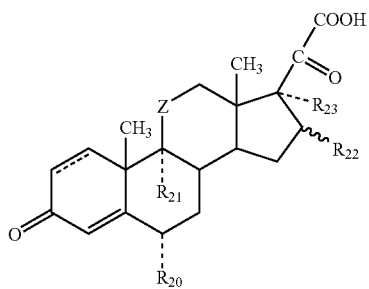

H wherein $R_{20}$ is hydrogen, fluoro, chloro, or methyl; $R_{21}$ is hydrogen, fluoro or chloro; $R_{22}$ is hydrogen, methyl, hydroxy or —$OCOR_{24}$ wherein $R_{24}$ is $C_1$-$C_7$ straight or branched alkyl or phenyl; $R_{23}$ is hydrogen, hydroxy, or —$OCOR_{24}$ wherein $R_{24}$ is as defined above, with the proviso that when $R_{22}$ is hydroxy or —$OCOR_{24}$ and $R_{23}$ is other than hydrogen, then $R_{22}$ and $R_{23}$ are identical; or $R_{22}$ and $R_{23}$ are combined to form a divalent radical of the type wherein $R_{25}$ and $R_{26}$, which can be the same or different are each $C_{1-7}$ straight or branched alkyl or phenyl; Z is carbonyl or β-hydroxymethylene; the wavy line at the 16-position indicates the α or β-configuration; and the dotted line in the ring A indicates that the 1,2-linkage is saturated or unsaturated; angiotension-converting enzyme inhibitors, such as (2R,4R)-2-(2-Hydroxyphenyl)-3-(3-mercaptopropionyl)-4-thiazolidinecarboxylic acid, Enalaprilic acid (N-[1-(S)-carboxy-3-phenyl-propyl]-L-alanyl-L-proline), Captopril, N-Cyclopentyl-N-[3-[(2,2-dimethyl-1-oxopropyl)thio]-2-methyl-1-oxopropyl]glycine, 1 [4-Carboxy-2-methyl-2R,4R-pentanoyl]-2,3-dihydro-2S-indole-2-carboxylic acid, Alecapril (1-[(S)-3-Acetylthio-2-methyl-propanoyl]-L-propyl-L-phenylalanine), [3 S-[2[R* (R*)]],3R*]-2-[2-[[1-carboxy-3-phenylpropyl]-amino]-1-oxopropyl]-1,2,3,4-tetrahydro-3-isoquinoline carboxylic acid, [2S-[1[R*(R*)]],2α,3α,7αβ]-[2-[[1-carboxy-3-phenylpropyl]-amino]-1-oxopropyl]octahydro-1H-indole-2-carboxylic acid; (S)-Benzamido-4-oxo-6-phenylhexanoyl-2-carboxypyrrolidine, Lisinopril, Tiopronin, Pivopril; and, other bioaffecting carboxylic acid agents, such as Ethacrynic acid, L-Tyrosine, α-Methyl-L-tyrosine, Penicillamine, Probenicid, 5-Aminosalicylic acid, 4-Aminobenzoic acid, Methyldopa, L-Dopa, Carbidopa, Valproic acid, 4-Aminobutyric acid, Moxalactam, Clavulanic acid, Tranexamic acid, Furosemide, 7-Theophylline acetic acid, Clofibric acid, Thienamycin, N-Formimidoylthienamycin, Amphotericin B, Nicotinic acid, Methotrexate, L-Thyroxine, Cromoglycic acid, Bumetanide, Folic acid, Chlorambucil, Melphalan, Fusidic acid, 4-Aminosalicylic acid, Liothyronine, Tretinoin, o-Thymotinic acid, 6-Aminocaproic acid, L-Cysteine, Tranilast (N-(3',4'-dimethoxycinnamoyl)anthranilic acid), Baclofen, 4-Amino-5-ethyl-3-thiophenecarboxylic acid, N-Cyclopentyl-N-[3-[(2,2-dimethyl-1-oxopropyl)thio]2-methyl-1-oxopropyl]glycine, Isoguvacine, Nipecotic acid, D-Eritadenine [(2R,3R)-4-adenin-9-yl-2,3-dihydroxybutanoic acid], (RS)-3-Adenin-9-yl-2-hydroxypropanoic acid, 1-[4-Carboxy-2-methyl-2R,4R-pentanoyl]-2,3-dihydro-2S-indole-2-carboxylic acid, Phenylalanylalanine, Glafenic acid, Floctafenic acid, N-(Phosphonoacetyl)-L-aspartic acid (PALA), Proxicromil, Cysteamine, N-Acetylcysteine, Proglumide, Aztreonam, Mecillinam, All-trans-retinoic acid, 13-cis-retinoic acid, Isonipecotic acid, Anthracene-9-carboxylic acid, α-Fluoromethylhistidine, 6-Amino-2-mercapto-5-methylpyrimidine-4-carboxylic acid, Glutathione, Acivicin, L-α-Glutamyl dopamine, 6-Aminonicotinic acid, Loflazepate, 6-[[1(S)-[3(S),4-dihydro-8-hydroxy-1-oxo-1H-2-benzopyran-3-yl]-3-methylbutyl]amino]-4-(S),5(S)-dihydroxy-6-oxo-3(S)-ammoniohexanoate, Z-2-Isovaleramidobut-2-enoic acid, D,L-2,4-Dihydroxyphenylalanine, L-2-Oxothiazolidine-4-carboxylic acid, Iopanoic acid, 4-Aminomethylbenzoic acid, 4-Hydroxybenzoic acid, 4-Hydroxybutyric acid, Ticrynafen, 4-amino-3-phenylbutyric acid, 4-(Dimethylamino)benzoic acid, Capobenic acid, Pantothenic acid, Folinic acid, Orotic acid, Biotin, Mycophenolic acid, Thioctic acid, Pyroglutamic acid, Oleic acid, Linoleic acid, Cholic acid, Naturally occurring amino acids (e.g. glycine, histidine, phenylalanine and glutamic acid), N,N-Dimethylglycine, Salazosulfapyridine, Azodisal, Isotretinoin and Etretinic acid.

Non-limiting examples of prostaglandins include: Prostaglandin $E_2$; Prostaglandin $F_{2\alpha}$; 15-Deoxy-16-hydroxy-16-vinylprostaglandin $E_2$; 11-Deoxy-11$_\alpha$,12$_\alpha$-methanoprostaglandin $E_2$; 11-Deoxy-11$_\alpha$,12$_\alpha$-difluoromethanoprostaglandin $E_2$; Prostacyclin; Epoprostenol; dl-16-Deoxy-16-hydroxy-16 ($\alpha/\beta$)-vinyl prostaglandin $E_2$; Prostaglandin $E_1$; Thromboxane $A_2$; 16,16-Dimethylprostaglandin $E_2$; (15R) 15-Methylprostaglandin $E_2$ (Arbaprostil); Meteneprost; Nileprost; and Ciprostene. Additional examples of prostaglandins can be found in U.S. Pat. No. 5,977,173 issued Nov. 2, 1999, U.S. Pat. No. 6,107,338 issued Aug. 22, 2000, U.S. Pat. No. 6,048,895 issued Apr. 11, 2000, U.S. Pat. No. 6,410,780 issued Jun. 25, 2002, U.S. Pat. No. 6,444,840 issued Sep. 3, 2002, U.S. Pat. No. 6,451,859 issued Sep. 17, 2002, Re-issue patent application Ser. No. 11/174,420 filed Jul. 1, 2005, U.S. patent application Ser. No. 09/774,555 filed Jan. 31, 2001, U.S. patent application Ser. No. 09/774,556 filed Jan. 31, 2001 and U.S. patent application Ser. No. 11/138,097 filed May 26, 2005, which are hereby fully incorporated by reference.

Preferred sugar alcohols suitable for use in preparing compounds of the invention include the C4 sugars threitol and erythritol, the C5 sugars arabinitol, xylitol, ribitol and lyxitol, and the C6 sugars glucitol, galactitol, mannitol, gulitol, altitol, allitol, iditol and talitol, more preferably, xylitol, ribitol, glucitol and mannitol. The invention includes the use of both D and L isomers. The sugar alcohol may also comprise at least one of 2-deoxyribitol, 2-deoxyglucitol, 2-deoxyxylitol.

Compositions

Compositions of the present invention comprise a safe and effective amount of one or more compounds of Formulas IA-C, one or more pharmaceutically acceptable salts of Formulas IA-C, or mixtures thereof. As used herein, "safe and effective amount" means an amount of a compound sufficient to significantly induce a positive modification in the condition to be treated, but low enough to avoid serious side effects (at a reasonable benefit/risk ratio), within the scope of sound medical judgment. A safe and effective amount of a compound will vary with the particular condition being treated, the age and physical condition of the patient being treated, the severity of the condition, the duration of the treatment, the nature of concurrent therapy, the particular pharmaceutically-acceptable carrier utilized, and like factors within the knowledge and expertise of the attending physician.

In addition to the compound, the compositions of the subject invention contain a pharmaceutically-acceptable carrier. The term "pharmaceutically-acceptable carrier", as used herein, means one or more compatible liquid, gel, cream or ointment diluents which are suitable for administration to a subject. The term "compatible", as used herein, means that the components of the composition are capable of being commingled with the compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the subject being treated. Some examples of substances which can serve as pharmaceutically-acceptable carriers or components thereof are gelatin, excipients, pyrogen-free water, isotonic saline, and phosphate buffer solutions. In one embodiment, the pharmaceutically acceptable carrier comprises an ophthalmically acceptable pharmaceutical excipient.

The choice of a pharmaceutically-acceptable carrier to be used in conjunction with a compound is basically determined by the way the compound is to be administered. The compounds of the present invention may be administered systemically. Routes of administration include transdermal; oral; parenterally, including subcutaneous or intravenous injection; topical; and/or intranasal.

The appropriate amount of the compound to be used may be determined by routine experimentation with animal models. Such models include, but are not limited to the intact and ovariectomized rat models, the ferret, rabbit, canine, and non human primate models as well as disuse models.

Suitable pharmaceutically-acceptable carriers for topical application include those suited for use in lotions, creams, gels, solutions, and the like. Advantageously, the composition is sterile and can be in dosage unit form, e.g., suitable for topical ocular use. The composition can be packaged in a form suitable for metered application, such as in container equipped with a dropper.

In a preferred embodiment, the composition is a solution prepared using a physiological saline solution as a carrier. The pH of the solution is, preferably, maintained between 4.5 and 8.0 using an appropriate buffer system. A neutral pH is more preferred. Compositions of the invention can also comprise pharmaceutically acceptable preservatives, stabilizers and/or surfactants.

In a further embodiment, the present invention relates to a method of treating glaucoma, or other disease or disorder of the eye related to elevated intraocular pressure. The method comprises administering to a mammal (e.g., a human) in need of such treatment an amount of the compound of Formulas IA-C, or pharmaceutically acceptable salt thereof, in an amount sufficient to effect the treatment. The dosing regimen can vary with the compound used, the patient and/or the effect sought. Selection of an optimum dosing regimen can be readily made by one skilled in the relevant art.

The invention may provide the means to achieve enhanced penetration and yet retain hydrolysis at a rate sufficient to treat disease, but to provide an assay to determine the optimal sugar alcohol to be attached to each drug.

It is recognized that not every possible combination of sugar alcohol and drug-containing carboxylic acid will have the optimum characteristics to ensure optimal delivery. To those skilled in the art, determining if the solubility imparted by the particular sugar alcohol is sufficient to meet the concentrations desired for disease treatment is straightforward. The test of corneal penetration and hydrolysis is much less straightforward.

In one aspect of this invention, a great advantage of this invention is the ease of determining which sugar alcohol ester is the most suitable candidate for in vivo dosing for each drug. Since the sugar alcohol moiety imparts water-solubility to the compounds, an assay can be readily set up to determine the optimal sugar alcohol for each drug moiety based on the release rate thus: A commercially-available preparation of esterase, such as porcine liver esterase (Sigma Corp., St. Louis), is prepared at a standard concentration. The drug-sugar alcohol combination, dissolved in methanol or a methanol-water or methanol-acetonitrile combination, is added dropwise to the esterase and the rate at which the compound is released from the alcohol is determined. The analytical technique used to determine the amount of free acid will vary with the acid used, but a typical procedure would be by TLC, or reverse-phase TLC, or HPLC or by Mass Spectroscopy. One skilled in the art can readily determine the optimal analytical method for each sugar-acid pair evaluated. This assay can easily be adapted to be run in a 96-well plate format, or other high-throughput method of determining activity.

The best candidates can then be taken to in vivo testing. In vivo pharmacological activity for glaucoma can be determined using assays designed to test the ability of the subject compounds to decrease intraocular pressure. Examples of such assays are described in the following reference, incorporated herein: C. Iiljebris, G. Selen, B. Resul, J. Sternschantz, and U. Hacksell, "Derivatives of 17-Phenyl-18,19,20-trinorprostaglandin Isopropyl Ester: Potential Antiglaucoma Agents", *Journal of Medicinal Chemistry*, Vol. 38 No. 2 (1995), pp. 289-304.

It is recognized that each drug and each disease state will have its own particular optimal delivery, and that one skilled in the art may modify the guidelines given herein. Combinations which are too quickly hydrolyzed offer no advantage over the free acids, and compounds which have no detectable hydrolysis in the assay are likewise not useful. It is the purpose of this invention to provide compounds which release their carboxcyclic acids under the conditions described, with a half-life of greater than one minute but less than seven days. A more preferred embodiment of the invention provides compounds that are released in greater than five minutes and less than 4 days, and still more preferred are compounds which are released in greater than five minutes and in less than 24 hours.

Certain aspects of the present invention are described in the non-limiting Examples that follow.

EXAMPLE 1

Preparation of 5-O-Ribitol [2,3-dichloro-4-(thiophene-2-carbonyl)]phenoxyacetate (Formula III), with reference to Scheme I.

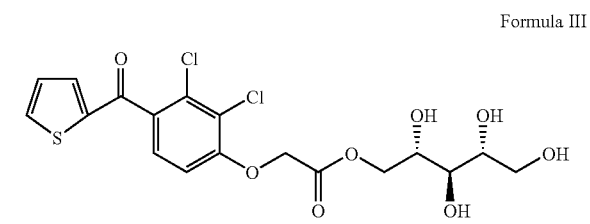 [SMILES: O=C(COc1ccc(C(=O)c2cccs2)c(Cl)c1Cl)OC[C@H](O)[C@H](O)[C@H](O)CO]

Formula III

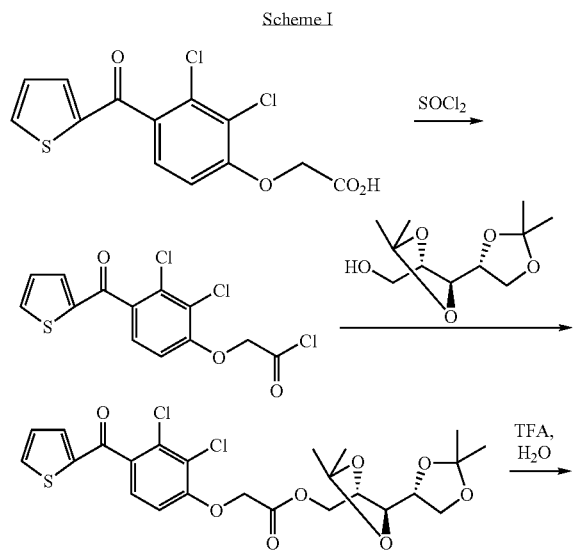

Scheme I

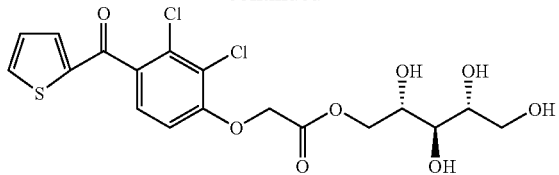

To a stirring suspension of ticrynafen (0.40 g, 1.2 mmol) in anhydrous benzene (1.5 mL) was added thionyl chloride (0.18 mL, 2 equiv) at room temperature. The reaction was heated to reflux, at which time all ticrynafen dissolved. Reflux was maintained for 2.5 h and the reaction was cooled and concentrated at reduced pressure. The residual oil was resuspended in anhydrous THF (2 mL), and added dropwise at room temperature to a stirring solution of 1,2:3,4-di-O-isoproylideneribitol (0.28 g), triethylamine (0.57 mL) in THF (1 mL). The reaction was stirred at room temperature for 16 h, concentrated at reduced pressure and resuspended in EtOAc (100 mL). This solution was extracted with water (2×50 mL) and brine (50 mL), and dried (anhydrous MgSO$_4$). The solvents were evaporated in vacuo, and the crude products were purified by flash chromatography (eluting with 25-50% EtOAc in hexane) to give the desired ester (0.266 g).

The ester obtained above (0.266 g) was dissolved in 90% aqueous trifluoroacetic acid (10 mL) at 0° C. After being stirred at 0° C. for 1 h, the reaction solution was concentrated at reduced pressure. Excess trifluoroacetic acid was removed by azeotropic distillation with dioxane at reduced pressure. The oily residue was purified by flash chromatography (eluting with 10% MeOH in DCM+0.1% triethylamine), affording 5-O-ribitol [2,3-dichloro-4-(thiophene-2-carbonyl)]phenoxyacetate (0.1 µg). $^1$H NMR (DMSO-d$_6$, 300 MHz) δ3.47 (m, 2H), 3.76 (dd, 1H), 3.84 (m, 1H), 3.96 (dd, 1H), 4.25 (m, 1H), 4.39 (t, 1H), 4.58 (t, 1H), 4.64 (d, 1H), 4.77 (d, 2H), 4.94 (d, 2H), 5.06 (s, 2H), 6.69 (d, 1H), 7.20 (d, 1H), 7.23 (d, 1H), 7.48 (d, 1H), 7.51 (d, 1H), 8.15 (d, 1H); $^{13}$CNMR (DMSO-d$_6$, 75 MHz) δ61.8, 63.1, 71.6, 72.0, 72.5, 72.6, 83.2, 112.0, 121.4, 127.8, 129.2, 129.7, 132.0, 136.8, 137.3, 142.8, 155.7, 168.0, 185.2; MS (FAB$^+$): m/z 465 (M+H$^+$).

EXAMPLE 2

Ticrynafen (Formula IV) is a drug of known activity against glaucoma. The free acid, as the carboxylate salt, has little or no activity presumably because penetration through the cornea into the anterior chamber is negligible. Simple esters of ticrynafen are highly insoluble and also show little or no activity. In contrast, the ribitol ester of ticrynafen (Formula III) is completely soluble in petrolatum/lanolin mixtures. The compound reduces intraocular pressure (IOP) in a dose-dependent fashion in Dutch-Belted white rabbits (see Example 3 and FIGS. 1-4).

Formula IV

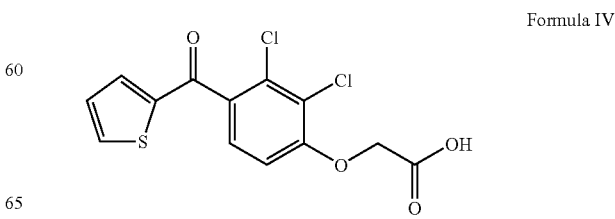

EXAMPLE 3

Ticrynafen-ribitol ester was formulated as an ointment in 5, 10, and 15% concentrations. The Dutch Belted rabbit model was used to test the formulation for both pressure lowering and side effects.

Baseline intraocular pressures were obtained by placing one drop of proparacaine in each eye followed by pressure measurements utilizing a Pneumotonometer®. One eye of each rabbit was then given 0.1 mg of ticrynafen-ribitol ester ointment topically in the inferior conjunctival sac. The second eye was used as a control with application of lanolin ointment without drug. Repeat doses were given at 24 hour intervals for a total of three doses (0, 24, and 48 hours). Intraocular pressures were recorded every 12 hours for one week. A total of twelve rabbits received the 5% ointment, eight rabbits the 10% ointment, and eight rabbits the 15% ointment.

Figure 2:
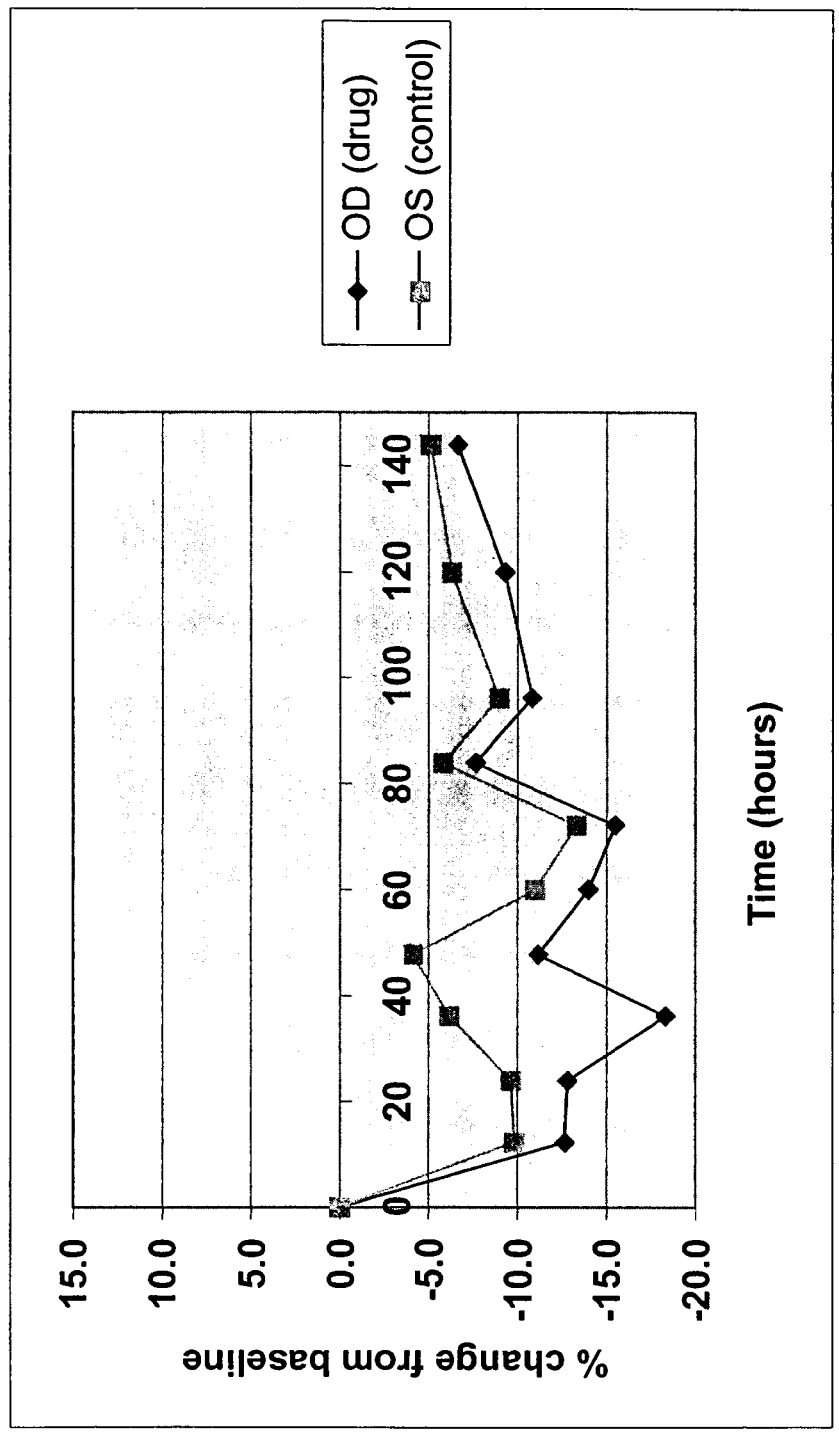
FIG. 2. Pressure reduction observed with 10% formulation of ticrynafen-ribitol ester.
Figure 3:
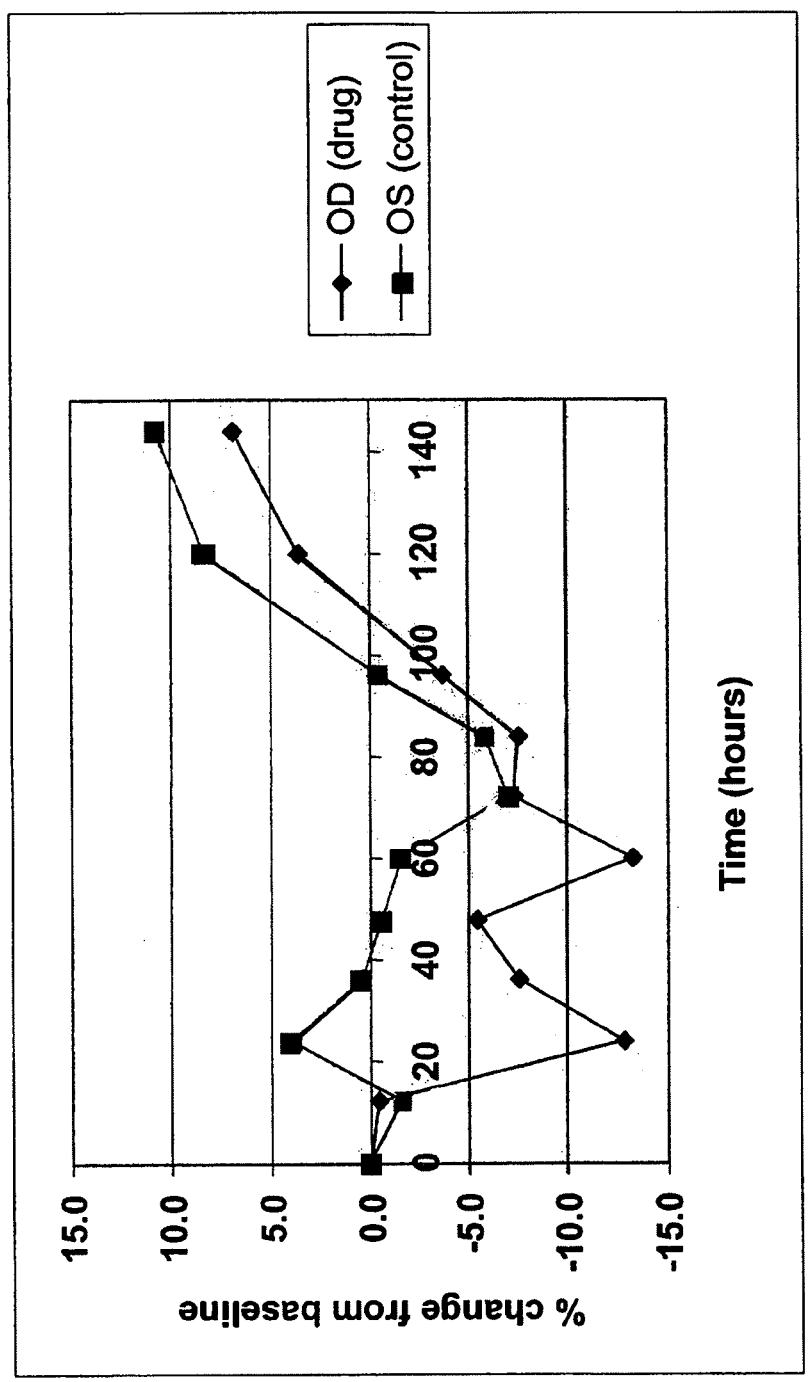
FIG. 3. Pressure reduction observed with 15% formulation of ticrynafen-ribitol ester.
Figure 4:
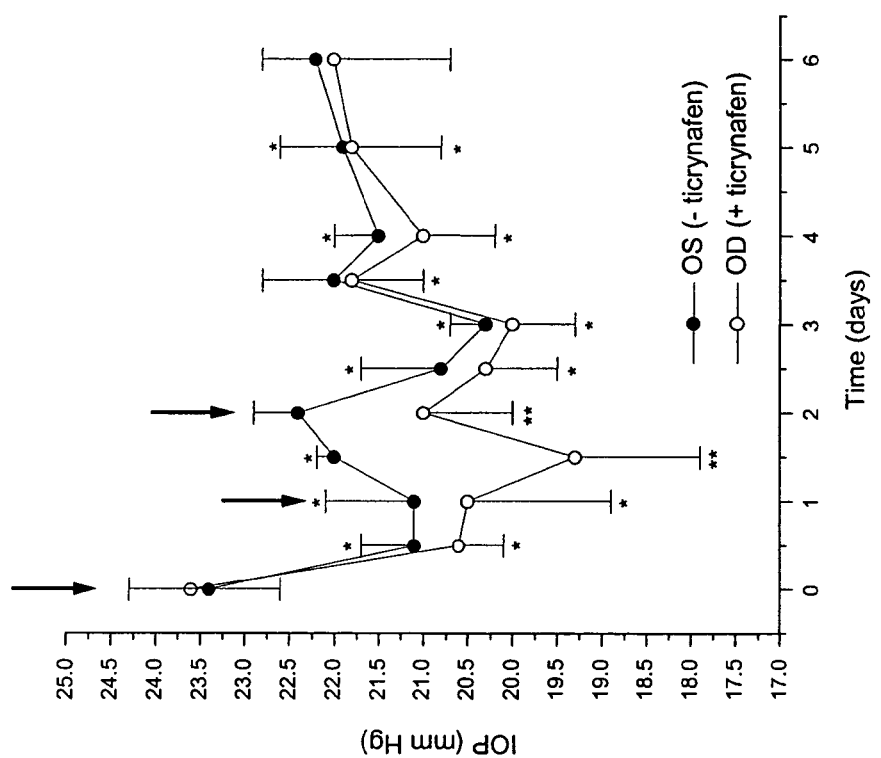
FIG. 4. Measurements of intraocular pressure in rabbits following treatment with ticrynafen-ribitol ester ointment (10% w/w). Arrows indicate the addition of ointment on days 1, 2, and 3. Data represent mean±standard error of the mean. Single asterisk indicates significant difference between present value and the value measured at time zero for each eye, $p<0.05$. Double asterisk indicates significant difference between OS (untreated) and OD (treated) eyes, $p<0.05$.

Pressure reduction for each concentration is shown in FIGS. 1, 2 and 3. FIG. 4 presents the 10% data with statistically significant timepoints indicated by double asterisks.

Maximal pressure reduction for each concentration is as follows:
  5% Ticrynafen-Ribitol ester: 11% at 54 hours
  10% Ticrynafen-Ribitol ester: 18% at 36 hours
  15% Ticrynafen-Ribitol ester: 13% at 60 hours

EXAMPLE 4

Preparation of 5-O-{(9α,11α,15R)-15-[2-Benzo[b]thiophen-2-yl]-16,17,18,19,20-pentanor-5,6,13,14-tetrahydro-9,11,15-trihydroxyprostanoyl}xylitol (Formula V), with reference to Scheme III.

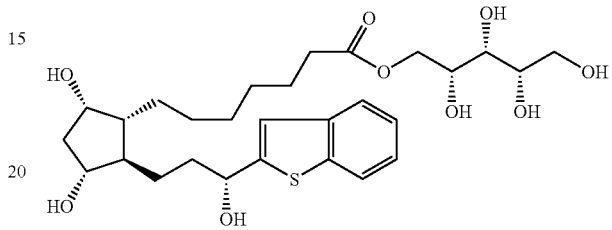

Formula V

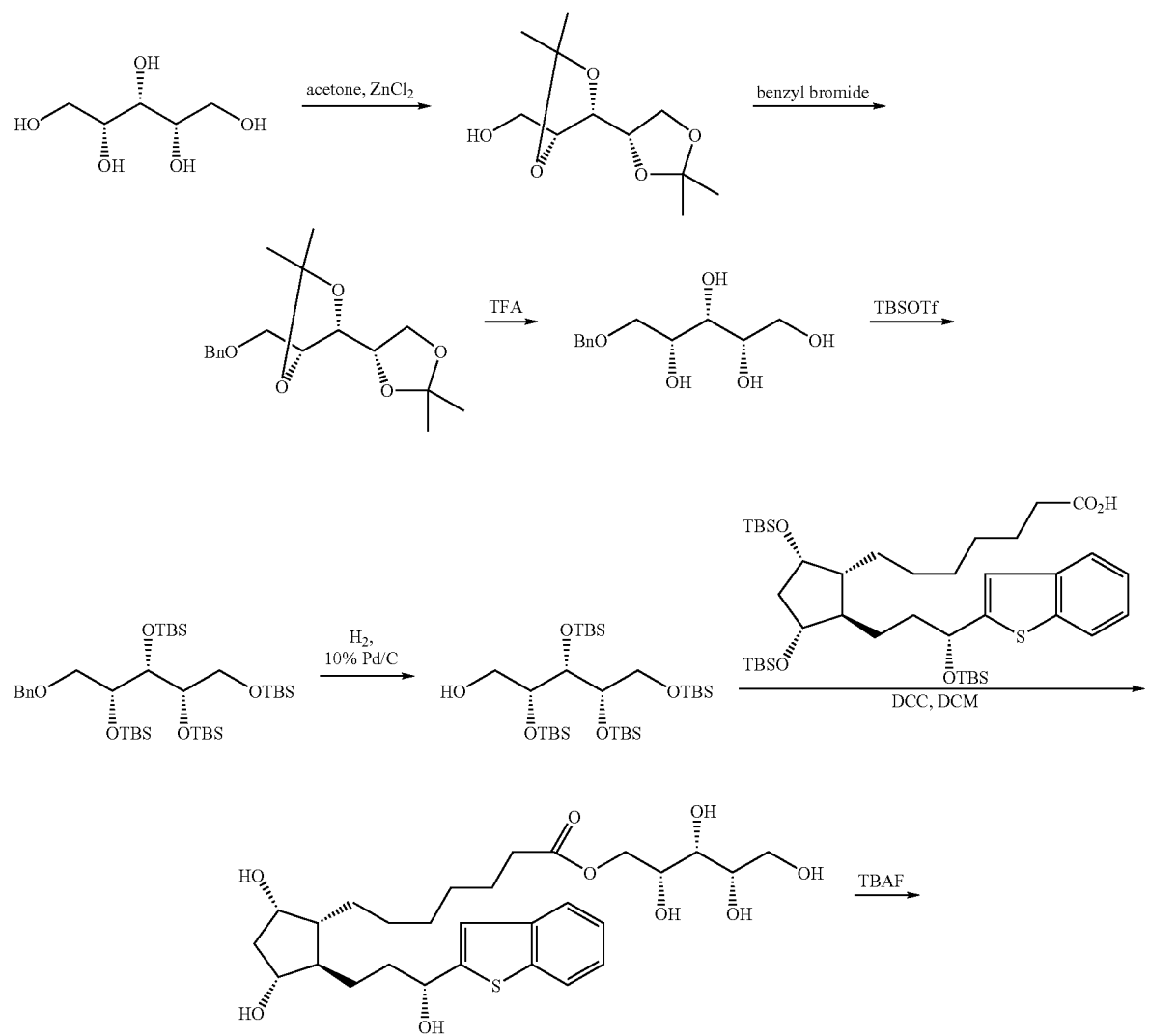

-continued

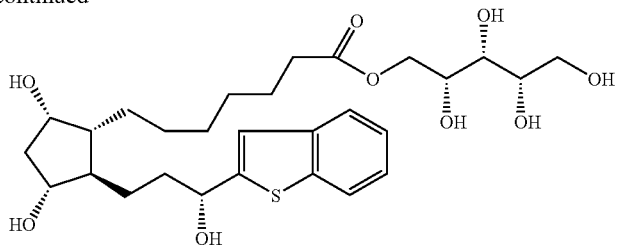

Zinc chloride (13.6 g, 100 mmol) was stirred with anhydrous acetone (110 mL) at room temperature for 15 min, and xylitol (7.6 g, 50 mmol) was added. After being stirred at room temperature for 24 h, the reaction solution was treated with 5N NaOH solution (180 mL), giving a two-phase solution with some white precipitates in the upper phase. The mixture was filtered off, and the filtrate was extracted with chloroform (4×100 mL). The combined extracts were washed with brine (2×60 mL), and dried over anhydrous $Na_2SO_4$. Evaporation of the solvents with rotary evaporator afforded the crude products (12 g). A portion (~3 g) of the crude products was purified by silica gel flash chromatography (eluting with 20-25% EtOAc in hexanes) to give 1,2:3,4-di-O-isoproylidenexylitol (1.6 g) as viscous oil, which crystallized on storage.

To an ice-cold stirred solution of 1,2:3,4-di-O-isoproylidenexylitol (2.4 g, 10 mmol) in anhydrous DMF (20 mL) was added 60% NaH (0.8 g, 20 mmol) in one portion. After the mixture was stirred at the same temperature for 1 h, benzyl bromide (3.56 mL, 30 mmol) was added at 0° C. in one portion. The whole mixture was stirred at 0° C. for 1 h, then at room temperature for additional 2 h. The reaction was quenched by adding ice-cold $H_2O$ (80 mL) at 0° C., and the resulting mixture was extracted with ether (3×100 mL). The ethereal extracts were washed with $H_2O$ (2×80 mL) and brine (80 mL), and dried over anhydrous $Na_2SO_4$. Evaporation of the solvents with rotary evaporator afforded the crude products, which was purified by silica gel flash chromatography (eluting with 10% EtOAc in hexanes) to give 5-benzyloxy-1,2:3,4-di-O-isopropylidene-xylitol (2.7 g, 83% yield) as viscous oil.

A trifluoroacetic acid/water solution (9:1 v/v, 5 mL) was added to 5-benzyloxy-1,2:3,4-di-O-isopropylidene-xylitol (640 mg, 2 mmol) at room temperature, and stirred at room temperature for 90 min. Then the dark brown solution was concentrated in vacuo to remove most of the solvents, followed by co-evaporated with toluene (2×20 mL). The residue was purified by silica gel flash chromatography (eluting with 0-10% MeOH in EtOAc) to give 5-benzyloxy xylitol (250 mg, 51% yield) as viscous oil.

2,6-Lutidine (0.93 mL, 8 mmol, 8 eq) was added dropwise to an ice-cold stirred solution of 5-benzyloxyxylitol (240 mg) in anhydrous DCM (10 mL), and tert-butyldimethylsilyl trifluoromethanesulfonate (TBDMSOTf) (1.38 mL, 6 mmol, 6 eq) was added dropwise. The mixture was stirred at 0° C. for 1 h, then allowed to warm to room temperature, and the stirring was continued for additional 14 h. The reaction mixture was diluted with EtOAc (150 mL), washed with 1N HCl aqueous solution (2×40 mL) and brine (2×50 mL), and dried over anhydrous $Na_2SO_4$. Evaporation of the solvents with rotary evaporator afforded the crude products, which was purified by silica gel flash chromatography (eluting with 5% EtOAc in hexanes) to give 5-benzyloxy-1,2,3,4-tetra(tert-butylydimethylsilyloxy)xylitol (650 mg, 93% yield) as viscous oil.

5-Benzyloxy-1,2,3,4-tetra(tert-butylydimethylsilyloxy) xylitol (600 mg, 0.86 mmol) dissolved in EtOAc (10 mL) was hydrogenated (balloon as $H_2$ container) in the presence of 10% Pd/C (100 mg) until no more the starting material could be detected on TLC plate (about 10 h). The catalyst was removed by filtration through a Celite pad, with rinsing the solid with EtOAc. The filtrate was evaporated to dryness, and the residue was purified by silica gel flash chromatography (eluting with 8% EtOAc in hexanes) to give 1,2,3,4-tetra(tert-butylydimethylsilyloxy)xylitol (330 mg, 63% yield) as white solid.

To a stirred solution of (9α,11α,15R)-15-[2-benzo[b]thiophen-2-yl]-16,17,18,19,20-pentanor-5,6,13,14-tetrahydro-9,11,15-tris(tert-butyldimethylsilyloxy)prostanoic acid (310 mg, 0.4 mmol) 1,2,3,4-tetra(tert-butyldimethylsilyloxy)xylitol (330 mg, 0.54 mmol), and DMAP (~10 mg) in anhydrous DCM (15 mL) was added N,N'-dicyclohexylcarbodiimide (DCC) (206 mg, 1 mmol), and the mixture was stirred at room temperature for 10 h. The resulting suspension was filtered off, and the filtrate was concentrated in vacuo, and purified by silica gel flash chromatography (eluting with 5% ether in hexanes) to give the ester (300 mg, 55% yield) as white solid.

Tetrabutylammonium fluoride (TBAF, 1.0M solution in THF) (3.1 mL, 3.1 mmol, 14 eq) was added to a stirred solution of the ester obtained above (300 mg, 0.22 mmol) in anhydrous THF (10 mL), and the solution was stirred at room temperature for 2 h. The solution was concentrated in vacuo, and the residue was purified by silica gel flash chromatography (eluting with 10% MeOH in EtOAc) to give 5-O-{(9α,11α,15R)-15-[2-benzo[b]thiophen-2-yl]-16,17,18,19,20-pentanor-5,6,13,14-tetrahydro-9,11,15-trihydroxyprostanoyl}xylitol (100 mg, 82% yield) as highly viscous oil. $^1H$ NMR (300 MHz, $CD_3OD$): δ1.27-2.10 (m, 18H), 2.30 (t, 2H, J=7.5 Hz), 3.60-4.19 (m, 9H), 4.96 (t, 1H, J=6.3 Hz), 7.20 (s, 1H), 7.25-7.35 (m, 2H), 7.68-7.80 (m, 2H); $^{13}C$ NMR (75 MHz, $CD_3OD$): δ24.81, 27.81, 28.22, 28.76, 28.99, 29.53, 33.84, 36.94, 42.80, 49.94, 51.08, 63.05, 65.60, 70.23, 70.24, 70.87, 72.55, 72.56, 77.36, 119.90, 122.17, 123.22, 123.84, 124.05, 139.50, 139.98, 150.47, 174.43; MS (FAB$^-$): m/z 553 (M−1).

EXAMPLE 5

The prostaglandin derivative shown in Formula II shows strong activity against glaucoma. The isopropyl ester of the Formula II compound is highly insoluble in aqueous solution (<0.001% in normal saline). In contrast, the xylitol ester shown in Formula V is soluble to at least 0.03% (see Example 6 for preparation). Furthermore, the compound shown in Formula V is readily hydrolyzed by pig liver esterase, strongly suggesting that the compound will be cleaved by endogenous esterases, releasing active drug.

EXAMPLE 6

The xylitol prostaglandin ester of Formula V (also called AR101) was formulated as a 0.004% solution for topical administration. The Dutch Belted Rabbit model was used to test the formulation for both pressure lowering and side effects.

Baseline intraocular pressures were obtained by placing one drop of proparacaine in each eye followed by pressure measurements with a Pneumotonometer®. One eye of each rabbit received a loading dose of 3 drops 0.004% AR101 on day 0 and day 10. One drop of AR101 was given daily on days 1-7 and 10-14. No drug was given on days 8 and 9. The contralateral control eye received balanced salt solution drops without AR101. Intraocular pressure measurements were recorded every 12 hours for two weeks.

Figure 5:
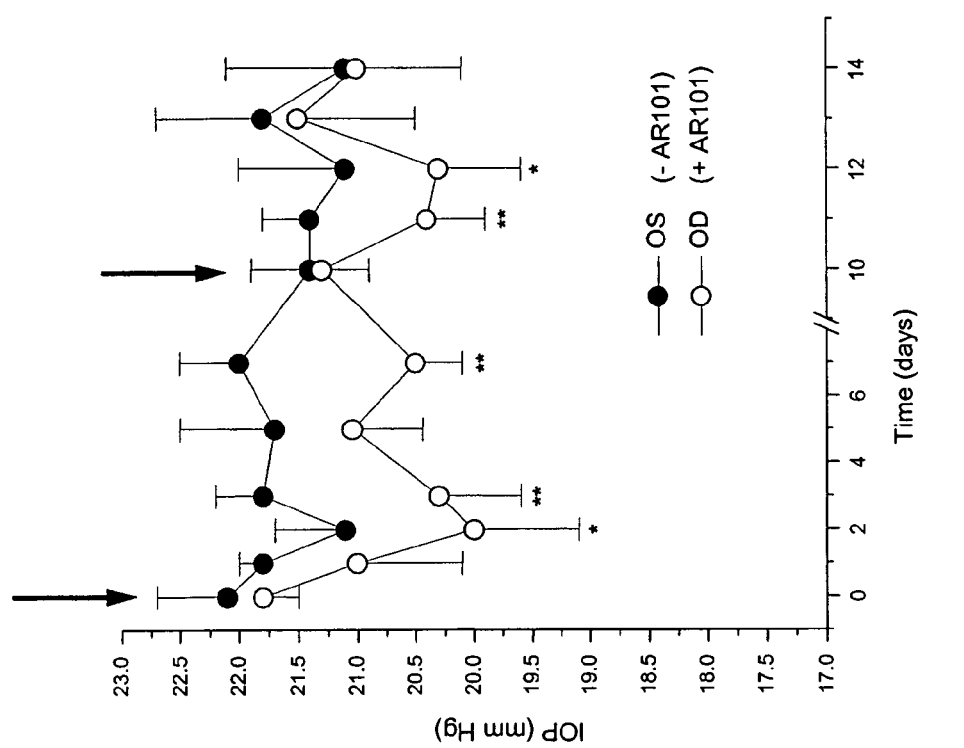
FIG. 5. Measurements of intraocular pressure in rabbits following daily treatments (1 drop) with AR101 (compound of Formula V). Arrows indicate the addition of a loading dose (3 drops) on day 0 and day 10. Animals were left untreated on days 8 and 9. Data represent mean±standard error of the mean. Single asterisk indicates significant difference between present value and the value measured at time zero for each eye, $p<0.05$. Double asterisk indicates significant difference between OS (untreated) and OD (treated) eyes, $p<0.05$.

FIG. 5 demonstrates pressure recordings for each eye. Statistically significant pressure reductions between eyes were observed on days 3, 7, and 11.

EXAMPLE 7

Preparation of 5-O-{(9α,11α,15R)-15-[2-Benzo[b]thiophen-2-yl]-16,17,18,19,20-pentanor-5,6,13,14-tetrahydro-9,11,15-trihydroxyprostanoyl}-D-ribitol (Formula VI), with reference to Scheme III.

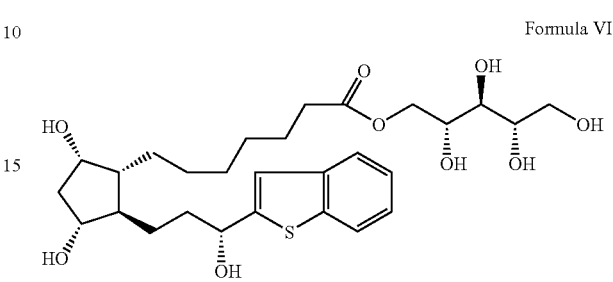

Formula VI

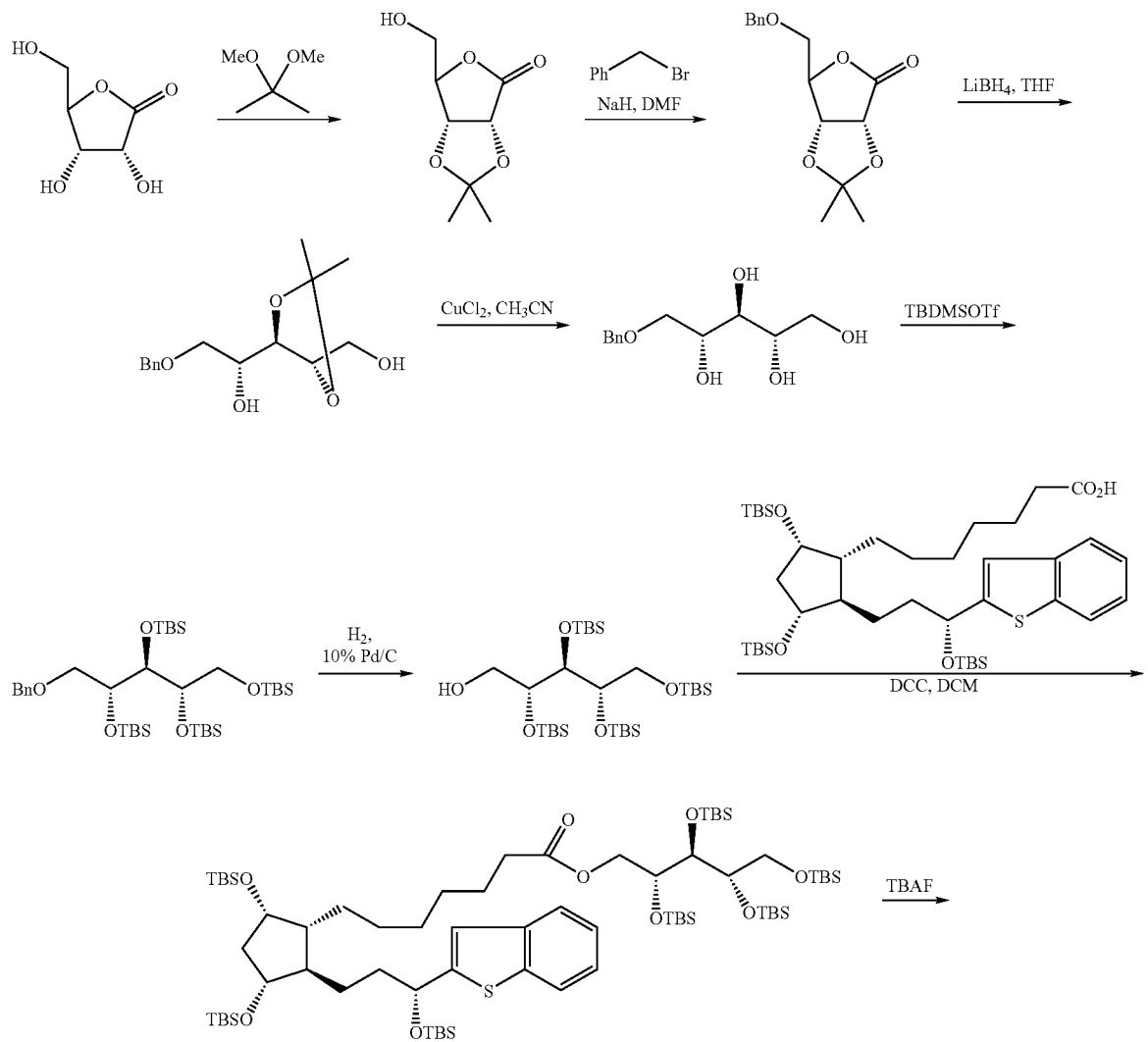

Scheme III

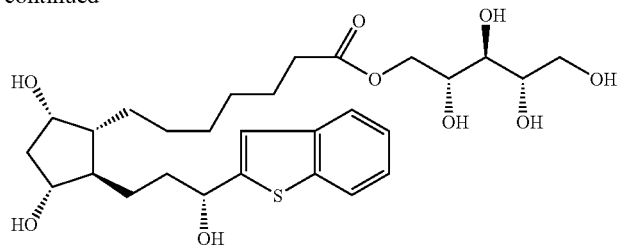

To a stirred solution of D-(+)-ribonolactone (9.93 g, 67 mmol) in anhydrous 2,2-dimethoxypropane (40 mL) was added pyridinium p-toluene-4-sulfonate (PPTS) (0.37 g), and the reaction mixture was heated with stirring at 50° C. for 1 h. After evaporation of the solvent with rotary evaporator, the oily residue was dissolved in EtOAc (300 mL), then washed with saturated NaHCO$_3$ (2×80 mL) and brine (2×80 mL), and dried (anhydrous Na$_2$SO$_4$). The solvent was evaporated with rotary evaporator, and the residue (14 g) was dissolved in THF (40 mL), and 1M HCl solution (10 mL) was added at room temperature. After being stirred at room temperature for 1 h, the reaction mixture was diluted with EtOAc (300 mL), then washed with saturated NaHCO$_3$ (2×80 mL) and brine (2×80 mL), and dried (anhydrous Na$_2$SO$_4$). The solvent was evaporated in vacuo to dryness, and the crude products were purified recrystallized from hexane/EtOAc, affording 2,3-O-isoproylidene-D-ribonolactone (8.2 g, 65% yield) as white crystal.

To an ice-cold stirred solution of 2,3-O-isoproylidene-D-ribonolactone (7.52 g, 40 mmol) in anhydrous DMF (30 mL) was added 60% NaH (1.92 g, 48 mmol) in one portion. After the mixture was stirred at the same temperature for 1 h, benzyl bromide (5.74 mL, 48 mmol) was added at 0° C. in one portion. The whole mixture was stirred at 0° C. for 1 h, then at room temperature for additional 17 h. The reaction was quenched by adding ice-cold H$_2$O (80 mL) at 0° C., and the resulting mixture was extracted with EtOAc (3×100 mL). The EtOAc extracts were washed with H$_2$O (100 mL) and brine (100 mL), and dried (anhydrous Na$_2$SO$_4$). Evaporation of the solvents with rotary evaporator afforded the crude products, which was purified by silica gel flash chromatography (eluting with 20% EtOAc in hexanes) to give 5-benzyloxy-2,3-O-isoproylidene-D-ribonolactone (9.4 g, 84% yield) as light-yellow oil.

2M LiBH$_4$ in THF solution (54 mL, 108 mmol) was added dropwise to a stirred solution of 5-benzyloxy-2,3-O-isoproylidene-D-ribonolactone (7.5 g, 27 mmol) in anhydrous THF (60 mL), and the reaction mixture was stirred at room temperature overnight (16 h). The reaction was quenched by adding brine (100 mL) at 0° C., and the resulting mixture was extracted with EtOAc (3×100 mL). The combined extracts were washed with brine (2×80 mL), and dried (anhydrous Na$_2$SO$_4$). Evaporation of the solvents in vacuo afforded the crude products, which was purified by silica gel flash chromatography (eluting with 50% EtOAc in hexanes) to give 5-benzyloxy-2,3-O-isoproylidene-D-ribitol (5.1 g, 67% yield) as an oil.

To a stirred solution of 5-benzyloxy-2,3-O-isoproylidene-D-ribitol (2.82 g, 10 mmol) in anhydrous acetonitrile (30 mL) was added CuCl$_2$.2H$_2$O (1.71 g, 10 mmol) at room temperature. After being stirred at room temperature for 3 h, the reaction solution was evaporated in vacuo to dryness, and the crude products were purified by silica gel flash chromatography (eluting with 0-9% MeOH in EtOAc) to give 5-benzyloxy-D-ribitol (2.4 g) as an green oil (contaminated with some copper salt).

2,6-Lutidine (7.0 mL, 60 mmol) was added dropwise to an ice-cold stirred solution of impure 5-benzyloxy-D-ribitol (2.4 g) in anhydrous DCM (90 mL), and tert-butyldimethylsilyl trifluoromethanesulfonate (TBDMSOTf) (11.5 mL, 50 mmol) was added dropwise at the same temperature. The mixture was stirred at 0° C. for 1 h, then allowed to warm to room temperature, and the stirring was continued for additional 14 h. The reaction mixture was diluted with EtOAc (220 mL), washed with 1N HCl solution (2×80 mL) and brine (3×80 mL), and dried (anhydrous Na$_2$SO$_4$). Evaporation of the solvents with rotary evaporator afforded the crude products, which was purified by silica gel flash chromatography (eluting with 5% EtOAc in hexanes) to give 5-benzyloxy-1,2,3,4-tetra(tert-butyldimethylsilyloxy)-D-ribitol (4.7 g, 67% yield based on 5-benzyloxy-2,3-O-isoproylidene-D-ribitol) as viscous oil.

5-Benzyloxy-1,2,3,4-tetra(tert-butyldimethylsilyloxy)-D-ribitol (4.5 g, 6.4 mmol) dissolved in EtOAc (80 mL) was hydrogenated (balloon as H$_2$ container) in the presence of 10% Pd/C (0.55 g) until no more starting material could be detected on TLC plate (about 3 h). The catalyst was removed by filtration through a Celite pad, with rinsing the solid with EtOAc. The filtrate was evaporated to dryness, and the residue was purified by silica gel flash chromatography (eluting with 5% EtOAc in hexanes) to give 1,2,3,4-O-tetra(tert-butyldimethylsilyl)-D-ribitol (3.8 g, 97% yield) as white solid.

To a stirred solution of (9α,11α,15R)-15-[2-benzo[b]thiophen-2-yl]-16,17,18,19,20-pentanor-5,6,13,14-tetrahydro-9,11,15-tris(tert-butyldimethylsilyloxy)prostanoic acid (305 mg, 0.4 mmol), 1,2,3,4-tetra(tert-butyldimethylsilyloxy)-D-ribitol (244 mg, 0.4 mmol) and DMAP (~10 mg) in anhydrous DCM (15 mL) was added N,N'-dicyclohexylcarbodiimide (DCC) (124 mg, 0.6 mmol), and the mixture was stirred at room temperature for 16 h. The resulting suspension was filtered off, and the filtrate was concentrated in vacuo, and purified by silica gel flash chromatography (eluting with 5% ether in hexanes) to give ester (300 mg, 55% yield) as an oil.

Tetrabutylammonium fluoride (TBAF, 1.0M solution in THF) (2.27 mL, 2.27 mmol) was added to a stirred solution of the ester obtained above (220 mg, 0.16 mmol) in anhydrous THF (10 mL), and the solution was stirred at room temperature for 3 h. The solution was concentrated in vacuo, and the residue was purified by silica gel flash chromatography (eluting with 10% MeOH in EtOAc) to give 5-O-{(9α,11α,15R)-15-[2-benzo[b]thiophen-2-yl]-16,17,18,19,20-pentanor-5,6,13,14-tetrahydro-9,11,15-trihydroxyprostanoyl}-D-ribitol (40 mg, 45% yield) as highly viscous oil. $^1$H NMR (300 MHz, CD$_3$OD): δ1.29-2.10 (m, 18H), 2.32 (t, 2H, J=7.5 Hz), 3.60-4.38 (m, 9H), 4.96 (t, 1H, J=6.3 Hz), 7.21 (s, 1H), 7.22-7.32 (m, 2H), 7.69-7.80 (m, 2H); $^{13}$C NMR (75 MHz, CD$_3$OD):

δ24.79, 27.79, 28.20, 28.74, 28.98, 29.51, 33.85, 36.92, 42.79, 49.92, 51.06, 63.32, 65.82, 70.29, 70.92, 72.46, 72.97, 77.33, 119.87, 122.13, 123.18, 123.81, 124.02, 139.49, 139.97, 150.45, 174.66.

EXAMPLE 8

Preparation of 4-O-{(9α,11α,15R)-15-[2-benzo[b]thiophen-2-yl]-16,17,18,19,20-pentanor-5,6,13,14-tetrahydro-9,11,15-trihydroxyprostanoyl}-L-threitol (Formula VII), with reference to Scheme IV.

Formula VII

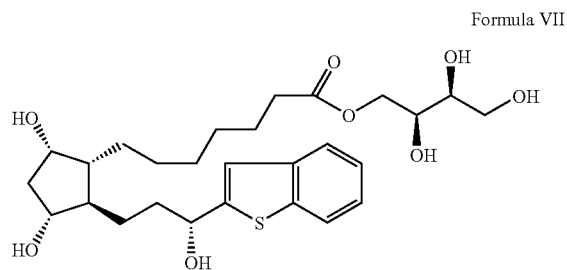 [SMILES: O=C(CCCCCC[C@@H]1[C@@H](CC[C@@H](O)c2cc3ccccc3s2)[C@H](O)C[C@@H]1O)OC[C@H](O)[C@@H](O)CO]

A solution of 2,3-O-isopropylidene-L-threitol (4.4 g, 27.2 mmol) in anhydrous DMF (20 mL) was added dropwise to an stirred solution (cooled to −15° C.) of 60% NaH (1.09 g, 27.2 mmol) in anhydrous DMF (30 mL), and the mixture was stirred at the same temperature for 30 min. Benzyl bromide (3.25 mL, 27.2 mmol) was added dropwise, and the whole mixture was stirred at −10--5° C. for 2 h. The reaction was quenched by adding ice-cold $H_2O$ (100 mL), and the resulting mixture was extracted with ether (3×100 mL). The ethereal extracts were washed with $H_2O$ (2×60 mL) and brine (60 mL), and dried (anhydrous $Na_2SO_4$). Evaporation of the solvents with rotary evaporator afforded the crude products, which was purified by silica gel flash chromatography (eluting with 25-33% EtOAc in hexanes) to give 4-benzyloxy-2,3-O-isoproylidene-L-threitol (3.9 g, 57% yield) as an oil.

To a stirred solution of 4-benzyloxy-2,3-O-isoproylidene-L-threitol (3.52 g, 14 mmol) in anhydrous acetonitrile (40 mL) was added $CuCl_2.2H_2O$ (4.8 g, 28 mmol) at room temperature. After being stirred at room temperature for 3 h, the reaction mixture was diluted with EtOAc (100 mL), and the suspension was filtered through a celite pad. The filtrate was evaporated in vacuo to dryness, and the crude products were purified by silica gel flash chromatography (eluting with EtOAc) to give 4-benzyloxy-L-threitol (3.5 g) as an green oil (contaminated with some copper salt).

2,6-Lutidine (7.0 mL, 60 mmol) was added dropwise to an ice-cold stirred solution of impure 4-benzyloxy-L-threitol (3.5 g) in anhydrous DCM (100 mL), and tert-butyldimethylsilyl trifluoromethanesulfonate (TBDMSOTf) (11.5 mL,

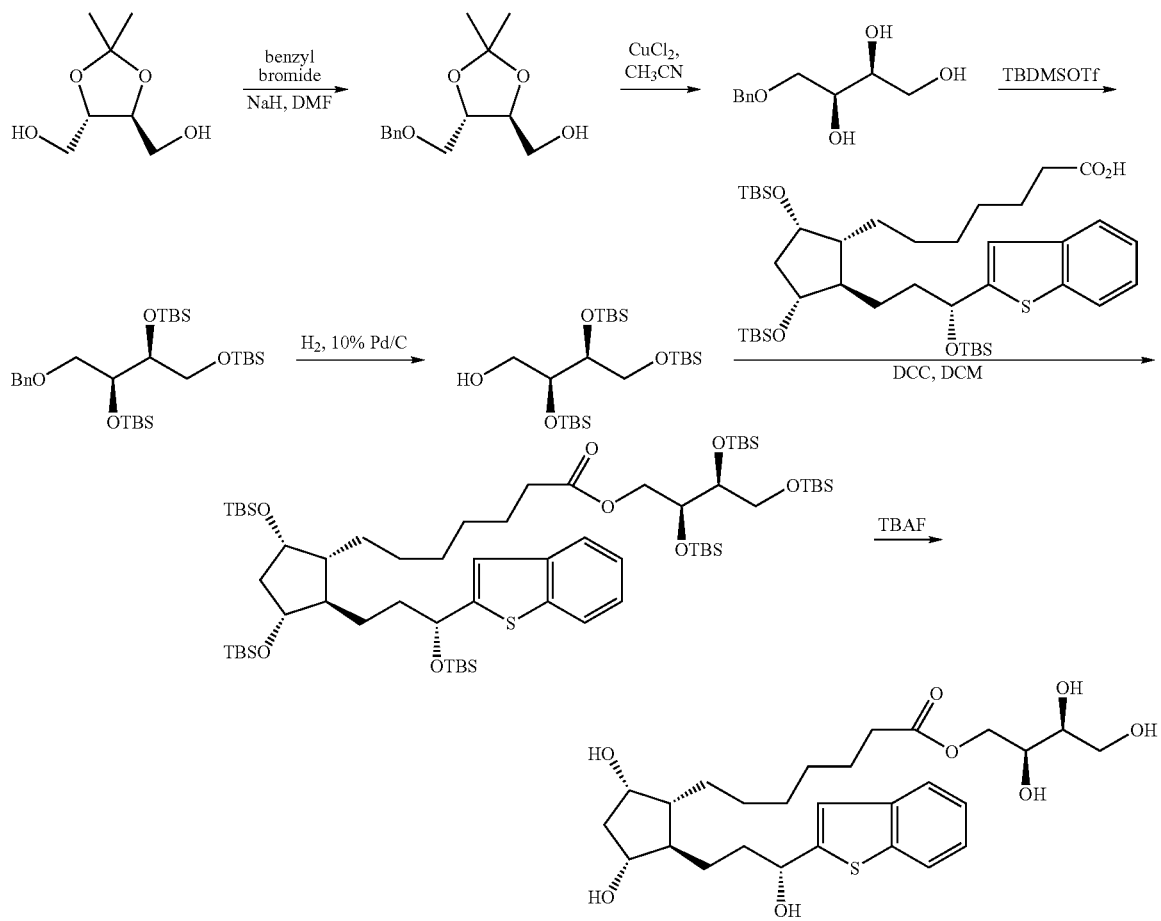

Scheme IV 50 mmol) was added dropwise at the same temperature. The mixture was stirred at 0° C. for 1 h, then allowed to warm to room temperature, and the stirring was continued for additional 14 h. The reaction mixture was diluted with EtOAc (200 mL), washed with 1N HCl solution (3×60 mL) H₂O (100 mL) and brine (100 mL), and dried (anhydrous Na₂SO₄). Evaporation of the solvents with rotary evaporator afforded the crude products, which was purified by silica gel flash chromatography (eluting with 5% ether in hexanes) to give 4-benzyloxy-1,2,3-tri(tert-butyldimethylsilyloxy)-L-threitol (6.0 g, 77% yield based on 4-benzyloxy-2,3-O-isoproylidene-L-threitol) as colorless oil.

4-Benzyloxy-1,2,3-tri(tert-butyldimethylsilyloxy)-L-threitol (5.9 g, 10.6 mmol) dissolved in EtOAc (70 mL) was hydrogenated (balloon as H₂ container) in the presence of 10% Pd/C (1 g) until no more starting material could be detected on TLC plate (about 5 h). The catalyst was removed by filtration through a Celite pad, with rinsing the solid with EtOAc. The filtrate was evaporated to dryness, and the residue was purified by silica gel flash chromatography (eluting with 10% ether in hexanes) to give 1,2,3-tri(tert-butyldimethylsilyloxy)-L-threitol (2.1 g, 41% yield).

To a stirred solution of (9α,11α,15R)-15-[2-benzo[b]thiophen-2-yl]-16,17,18,19,20-pentanor-5,6,13,14-tetrahydro-9,11,15-tris(tert-butyldimethylsilyloxy)prostanoic acid (305 mg, 0.4 mmol), 1,2,3-tri(tert-butyldimethylsilyloxy)-L-threitol (232 mg, 0.5 mmol) and DMAP (~10 mg) in anhydrous DCM (15 mL) was added N,N'-dicyclohexylcarbodiimide (DCC) (165 mg, 0.8 mmol), and the mixture was stirred at room temperature for 12 h. The resulting suspension was filtered off, and the filtrate was concentrated in vacuo, and purified by silica gel flash chromatography (eluting with 5% ether in hexanes) to give ester (236 mg, 49% yield) as oil.

Tetrabutylammonium fluoride (TBAF, 1.0M solution in THF) (2.28 mL, 2.28 mmol) was added to a stirred solution of the ester obtained above (230 mg, 0.19 mmol) in anhydrous THF (10 mL), and the solution was stirred at room temperature for 3 h. The solution was concentrated in vacuo, and the residue was purified by silica gel flash chromatography (eluting with 10% MeOH in EtOAc) to give 4-O-{(9α,11α,15R)-15-[2-benzo[b]thiophen-2-yl]-16,17,18,19,20-pentanor-5,6,13,14-tetrahydro-9,11,15-trihydroxyprostanoyl}-L-threitol (60 mg, 60% yield) as highly viscous oil. ¹H NMR (300 MHz, CD₃OD): δ1.22-2.10 (m, 18H), 2.31 (t, 2H, J=7.2 Hz), 3.50-4.16 (m, 8H), 4.96 (t, 1H, J=6.6 Hz), 7.21 (s, 1H), 7.22-7.32 (m, 2H), 7.69-7.80 (m, 2H); ¹³C NMR (75 MHz, CD₃OD): δ24.81, 27.80, 28.20, 28.75, 28.98, 29.51, 33.84, 36.93, 42.79, 49.92, 51.07, 62.92, 65.52, 69.24, 70.31, 71.81, 72.45, 77.35, 119.89, 122.15, 123.20, 123.83, 124.04, 139.50, 139.98, 150.46, 174.41.

EXAMPLE 9

Preparation of 5-O-Xylitol 4-(2-phenylacryloyl)cinnamate (Formula VIII), with reference to Scheme V.

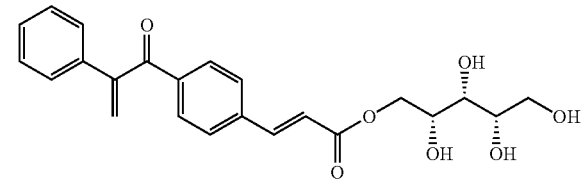

Formula VIII

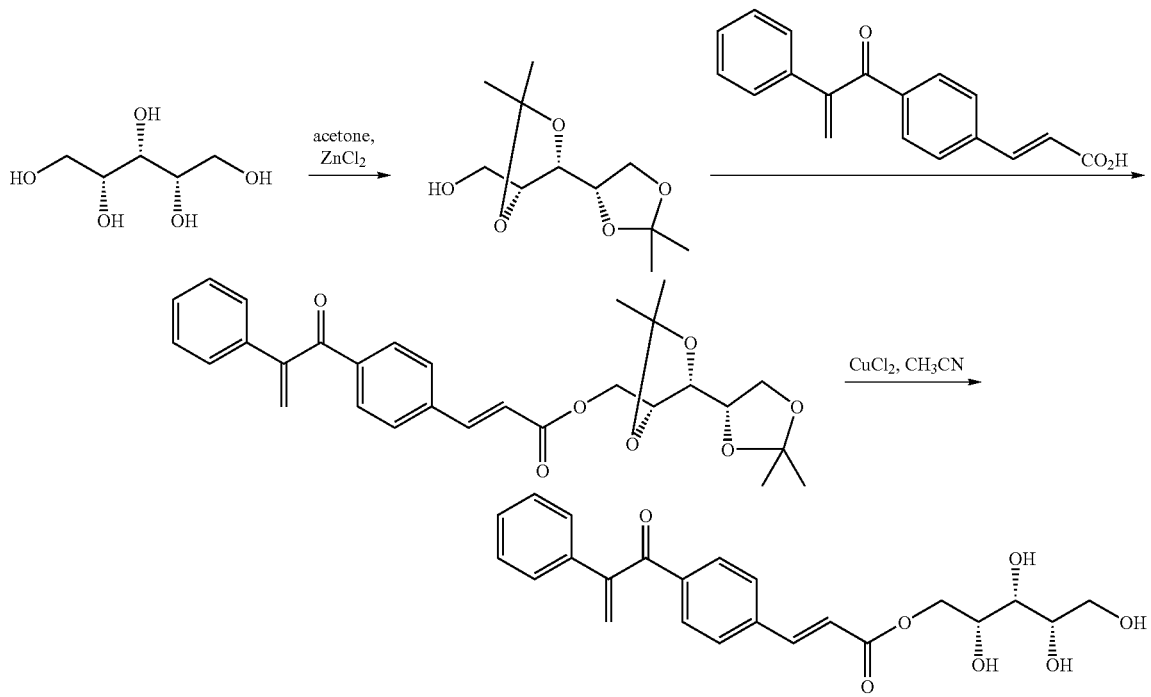

Scheme V

Zinc chloride (13.6 g, 100 mmol) was stirred with anhydrous acetone (110 mL) at room temperature for 15 min, and xylitol (7.6 g, 50 mmol) was added. After being stirred at room temperature for 24 h, the reaction solution was treated with 5N NaOH solution (180 mL), giving a two-phase solution with some white precipitates in the upper phase. The mixture was filtered off, and the filtrate was extracted with chloroform (4×100 mL). The combined extracts were washed with brine (2×60 mL), and dried over anhydrous $Na_2SO_4$. Evaporation of the solvents with rotary evaporator afforded the crude products (12 g). A portion (~3 g) of the crude products was purified by silica gel flash chromatography (eluting with 20-25% EtOAc in hexanes) to give 1,2:3,4-di-O-isoproylidenexylitol as viscous oil (1.6 g), which crystallized on storage.

To a stirred solution of 4-(2-phenylacryloyl)cinnamic acid (1.11 g, 4 mmol), 1,2:3,4-di-O-isoproylidenexylitol (0.93 g, 4 mmol) and DMAP (0.05, 0.4 mmol) in anhydrous DCM (60 mL) was added N,N'-dicyclohexylcarbodiimide (DCC) (1.24 g, 6 mmol), and the mixture was stirred at room temperature for 4 h. The resulting yellow suspension was filtered off, and the filtrate was concentrated in vacuo, and purified by silica gel flash chromatography (eluting with 25% EtOAc in hexanes) to give ester (1.5 g, 76% yield).

To a stirred solution of the ester obtained above (0.84 g, 1.7 mmol) in anhydrous acetonitrile (20 mL) was added $CuCl_2.2H_2O$ (1.16 g, 6.8 mmol) at room temperature. After being stirred at room temperature for 7 h, the reaction mixture was diluted with EtOAc (200 mL), washed with brine (3×50 mL), and dried. The solution was evaporated in vacuo to dryness, and the crude products were purified by silica gel flash chromatography (eluting with 5% MeOH in EtOAc) to give 5-O-xylitol 4-(2-phenylacryloyl)cinnamate (0.4 g, 57% yield) as light-yellow soft solid. $^1H$ NMR (300 MHz, $CD_3OD$): δ3.60-4.33 (m, 7H), 5.63 (s, 1H), 6.12 (s, 1H), 6.65 (d, 1H, J=16.2 Hz), 7.31-7.40 (m, 5H), 7.68 (d, 2H, J=8.4 Hz), 7.73 (d, 1H, J=16.2 Hz), 7.89 (d, 2H, J=8.4 Hz); $^{13}C$ NMR (75 MHz, $CD_3OD$): δ63.00, 66.08, 70.27, 70.92, 72.52, 120.54, 120.90, 126.95, 128.13, 128.44, 128.57, 130.33, 137.10, 138.22, 139.19, 143.51, 148.64, 166.84, 197.41; MS ($FAB^+$): m/z 413 (M+1).

EXAMPLE 10

Preparation of 1-O-D-Sorbitol 4-(2-phenylacryloyl)cinnamate (Formula IX), with reference to Scheme VI.

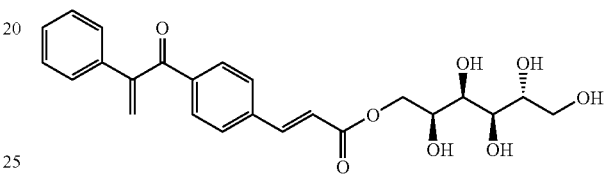

Formula IX

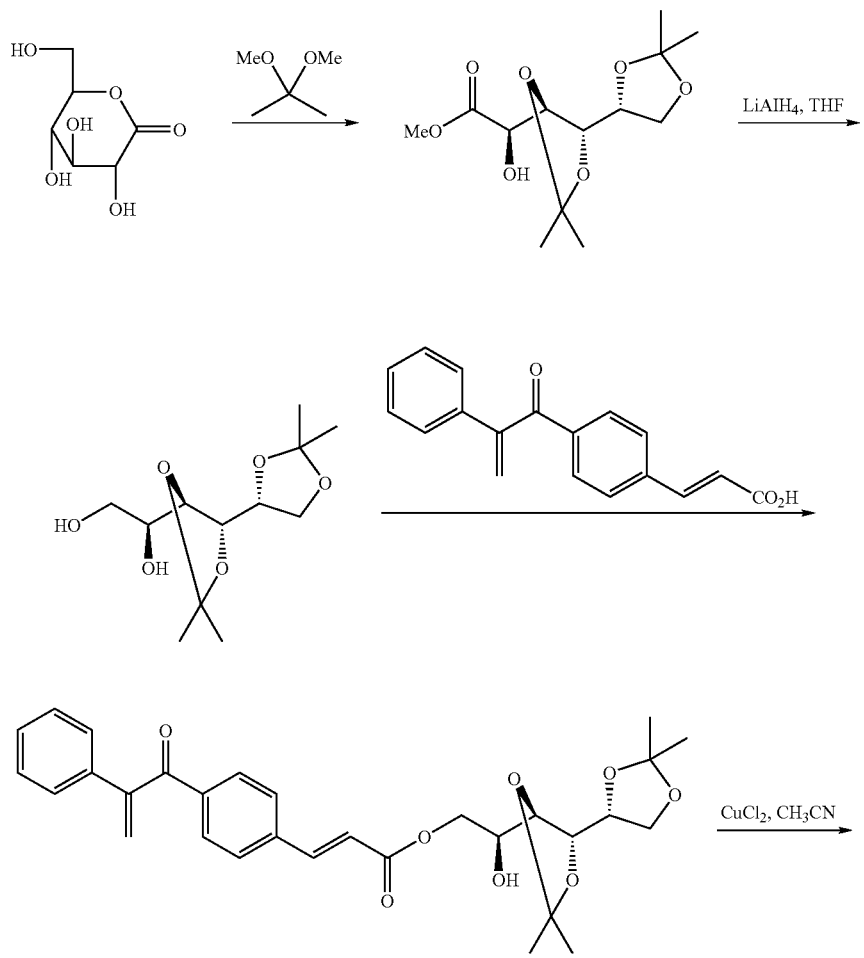

Scheme VI

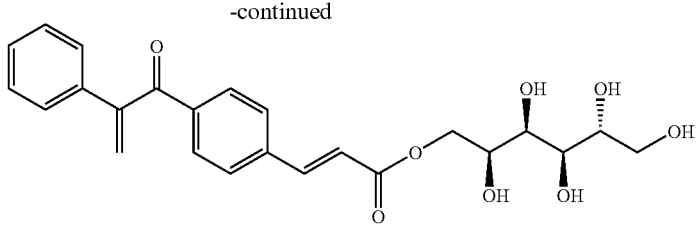

10

A mixture of D-glucono-1,5-lactone (17.8 g, 100 mmol), anhydrous 2,2-dimethoxypropane (30 mL), anhydrous acetone (10 mL), anhydrous MeOH (3 mL) and PTSA (0.2 g) was stirred at room temperature for 48 h. The reaction was quenched by adding saturated NaHCO$_3$ (100 mL). The resulting mixture was extracted with EtOAc (3×100 mL), washed with brine (2×50 mL), and dried (anhydrous Na$_2$SO$_4$). Evaporation of the solvents with rotary evaporator afforded the crude products (26 g), which was purified by silica gel flash chromatography (eluting with 20-25% EtOAc in hexanes) to give 3,4:5,6-di-O-isopropylidene-D-gluconic acid methyl ester (18 g, 62% yield).

To a stirred solution of 3,4:5,6-di-O-isopropylidene-D-gluconic acid methyl ester (8.0 g, 27.5 mmol) in anhydrous THF (30 mL) was added slowly 1M LiAlH$_4$ THF solution (36.3 mL, 36.3 mmol) at room temperature, and the mixture was heated at 75° C. for 15 h. After being cooled to 0° C., the reaction mixture was treated with saturated potassium sodium tartrate solution (5 mL). The resulting suspension was diluted with brine (100 mL) and EtOAc (200 mL). The organic layer was separated, and the aqueous layer was extracted with EtOAc (2×100 mL). The combined organic layers were washed with brine (60 mL), and dried (anhydrous Na$_2$SO$_4$). The solvents were evaporated in vacuo, and the crude products were purified by silica gel flash chromatography (eluting with 30-70% EtOAc in hexanes) to give 3,4:5,6-di-O-isopropylidene-D-sorbitol (6.2 g, 86% yield).

To an ice-cold stirred solution of 4-(2-phenylacryloyl)cinnamic acid (278 mg, 1 mmol), 3,4:5,6-di-O-isopropylidene-D-sorbitol (262 mg, 1 mmol) and DMAP (~10 mg) in anhydrous DCM (20 mL) was added N,N'-dicyclohexylcarbodiimide (DCC) (185 mg, 0.9 mmol), and the mixture was stirred at the same temperature for 3 h. The resulting yellow suspension was filtered off, and the filtrate was concentrated in vacuo, and purified by silica gel flash chromatography (eluting with 25% EtOAc in hexanes) to give ester (320 mg, 61% yield).

To a stirred solution of the ester obtained above (310 mg, 0.6 mmol) in anhydrous acetonitrile (10 mL) was added CuCl$_2$.2H$_2$O (511 mg, 3 mmol) at room temperature. After being stirred at room temperature for 7 h, the reaction mixture was diluted with EtOAc (100 mL), washed with brine (2×50 mL), and dried. The solution was evaporated in vacuo to dryness, and the crude products were purified by silica gel flash chromatography (eluting with 5% MeOH in EtOAc) to give 1-O-D-sorbitol 4-(2-phenylacryloyl)cinnamate (160 mg, 60% yield) as white solid. $^1$H NMR (300 MHz, DMSO-d$_6$): δ3.45-4.50 (m, 8H), 5.62 (s, 1H), 6.20 (s, 1H), 6.73 (d, 1H, J=15.9 Hz), 7.30-7.40 (m, 7H), 7.70 (d, 1H, J=16.2 Hz), 7.84 (m, 2H); MS (FAB$^+$): m/z 443 (M+1).

EXAMPLE 11

Preparation of 1-O-D-Arabitol 4-(2-phenylacryloyl)cinnamate (Formula X), with reference to Scheme VII.

Formula X

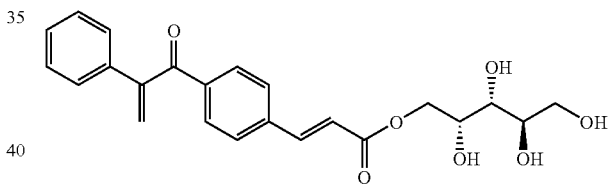

Scheme VII

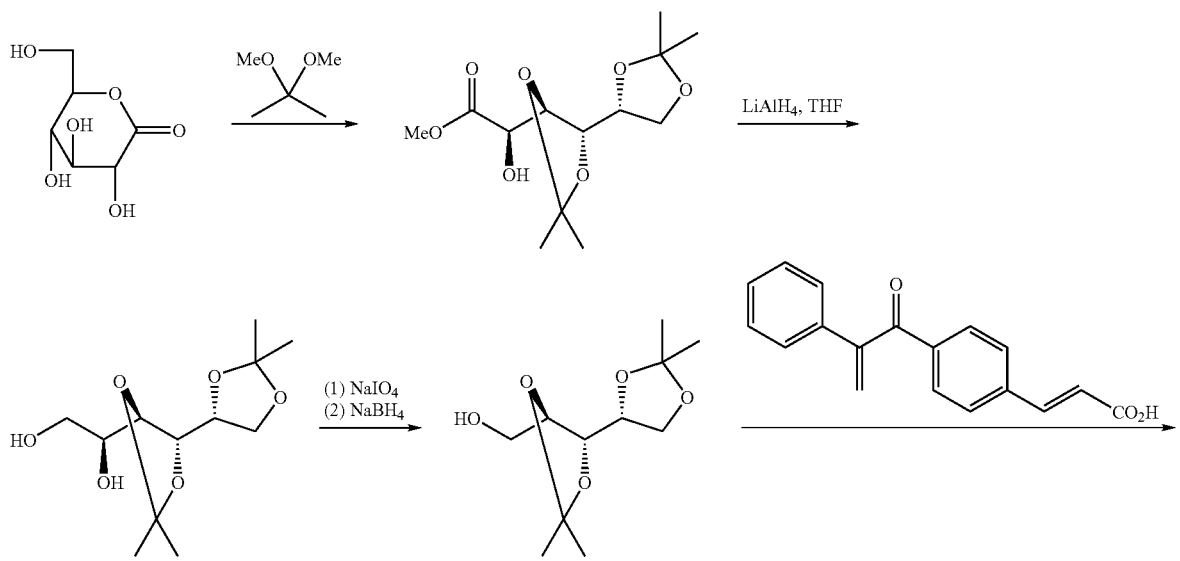

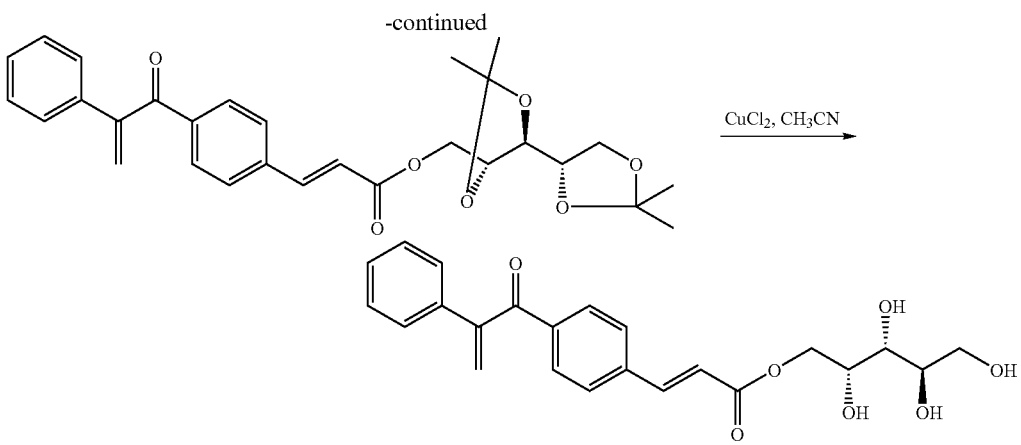

A mixture of D-glucono-1,5-lactone (17.8 g, 100 mmol), anhydrous 2,2-dimethoxypropane (30 mL), anhydrous acetone (10 mL), anhydrous MeOH (3 mL) and PTSA (0.2 g) was stirred at room temperature for 48 h. The reaction was quenched by adding saturated NaHCO$_3$ (100 mL). The resulting mixture was extracted with EtOAc (3×100 mL), washed with brine (2×50 mL), and dried (anhydrous Na$_2$SO$_4$). Evaporation of the solvents with rotary evaporator afforded the crude products (26 g), which was purified by silica gel flash chromatography (eluting with 20-25% EtOAc in hexanes) to give 3,4:5,6-di-O-isopropylidene-D-gluconic acid methyl ester (18 g, 62% yield).

To a stirred solution of 3,4:5,6-di-O-isopropylidene-D-gluconic acid methyl ester (8.0 g, 27.5 mmol) in anhydrous THF (30 mL) was added slowly 1M LiAlH$_4$ THF solution (36.3 mL, 36.3 mmol) at room temperature, and the mixture was heated at 75° C. for 15 h. After being cooled to 0° C., the reaction mixture was treated with saturated potassium sodium tartrate solution (5 mL). The resulting suspension was diluted with brine (100 mL) and EtOAc (200 mL). The organic layer was separated, and the aqueous layer was extracted with EtOAc (2×100 mL). The combined organic layers were washed with brine (60 mL), and dried (anhydrous Na$_2$SO$_4$). The solvents were evaporated in vacuo, and the crude products were purified by silica gel flash chromatography (eluting with 30-70% EtOAc in hexanes) to give 3,4:5,6-di-O-isopropylidene-D-sorbitol (6.2 g, 86% yield).

To a stirred mixture of 3,4:5,6-di-O-isopropylidene-D-sorbitol (3.0 g, 11.4 mmol) in H2O (35 mL) was added NaIO4 (3.0 g, 14 mmol) was added at room temperature, and the mixture was stirred at room temperature for 4 h. The resulting colorless solution was saturated by adding solid NaCl (~10 g), then extracted with DCM (370 mL), washed with brine (60 mL), and dried. Evaporation of the solvents in vacuo afforded the crude aldehyde (2.2 g).

The crude aldehyde (2.2 g) was dissolved in MeOH (30 mL), and cooled to 0° C. NaBH$_4$ (0.3 g, 8.7 mmol) was added, and the reaction mixture was stirred at 0° C. for 90 min. The reaction was quenched by adding brine (80 mL), extracted with DCM (2100 mL), and dried. The solvents were evaporated in vacuo, and the crude products were purified by silica gel flash chromatography (eluting with 25% EtOAc in hexanes) to give 2,3:4,5-di-O-isopropylidene-D-arabitol (2.1 g, 79% yield based on 3,4:5,6-di-O-isopropylidene-D-sorbitol).

To a stirred solution of 4-(2-phenylacryloyl)cinnamic acid (556 mg, 2 mmol), 2,3:4,5-di-O-isopropylidene-D-arabitol (464 mg, 2 mmol) and DMAP (~25 mg) in anhydrous DCM (30 mL) was added N,N'-dicyclohexylcarbodiimide (DCC) (618 mg, 3 mmol), and the mixture was stirred at room temperature for 4 h. The resulting suspension was filtered off, and the filtrate was concentrated in vacuo, and purified by silica gel flash chromatography (eluting with 25% EtOAc in hexanes) to give an ester (780 mg, 79% yield).

To a stirred solution of the ester obtained above (720 mg, 1.46 mmol) in anhydrous acetonitrile (20 mL) was added CuCl$_2$.2H$_2$O (1.0 g, 5.9 mmol) at room temperature. After being stirred at room temperature for 10 h, the reaction mixture was diluted with EtOAc (100 mL), and the suspension was filtered through suction. The solid was washed with H$_2$O (50 mL) and brine (2×50 mL), and air-dried. The white solid 1-O-D-arabitol 4-(2-phenylacryloyl)cinnamate (500 mg, 83% yield) was collected. $^1$H NMR (300 MHz, DMSO-d$_6$): δ3.40-4.40 (m, 7H), 5.62 (s, 1H), 6.19 (s, 1H), 6.74 (d, 1H, J=15.9 Hz), 7.30-7.44 (m, 7H), 7.69 (d, 1H, J=16.2 Hz), 7.83 (m, 2H); $^{13}$C NMR (75 MHz, DMSO-d$_6$): δ64.22, 67.02, 68.02, 71.35, 71.68, 121.68, 127.53, 129.24, 129.40, 130.68, 137.17, 138.23, 139.30, 143.60, 147.84, 166.60, 197.03; MS (FAB$^+$): m/z 413 (M+1).

EXAMPLE 12

Preparation of 1-O-Glycerol [2,3-dichloro-4-(2-methylenebutyryl)]phenoxyacetate (Formula XI), with reference to Scheme VIII.

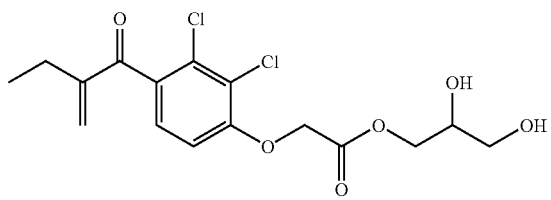

Formula XI

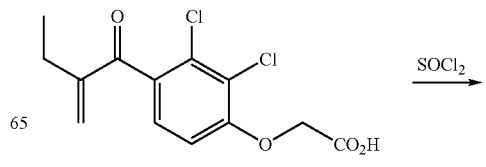

Scheme VIII

-continued

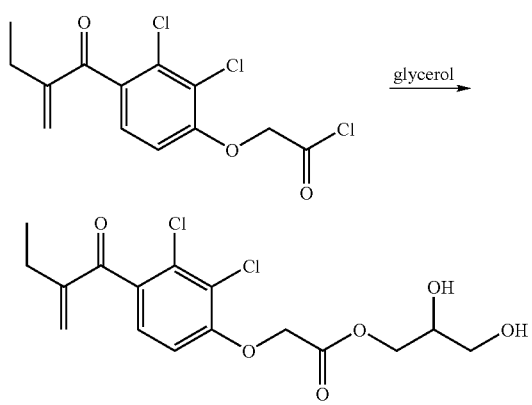

-continued

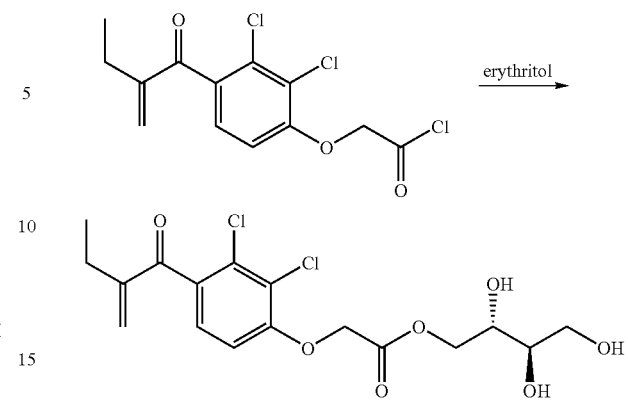

Ethacrynic acid (0.5 g, 1.65 mmol) was suspended in benzene (3.0 mL) and thionyl chloride (0.25 mL, 2 equiv), and heated to reflux for 1.5 h. The reaction was cooled to room temperature and concentrated under reduced pressure. The residue was dissolved in diethyl ether (5 mL) and added to a refluxing suspension of glycerol (2 mL) in diethyl ether (3.0 mL). The reaction was stirred at reflux for 3 h. After cooled to room temperature, the reaction solution was concentrated in vacuo. The residue was dissolved in DCM (50 mL), washed with water and saturated NaHCO$_3$. The organic phase was dried over anhydrous MgSO$_4$, filtered and concentrated in vacuo. The crude products were purified by column chromatography (eluting with 15:1 EtOAc/MeOH) to give 1-O-glycerol [2,3-dichloro-4-(2-methylenebutyryl)-phenoxyacetate. IR: 3400, 2967, 2937, 1758, 1664, 1585, 1202 cm$^{-1}$; $^1$H NMR (CDCl$_3$, 300 MHz): δ1.06 (t, 2H), 2.39 (q, 2H), 3.98-3.38 (m, 6H), 4.20 (d, 2H), 4.77 (s, 2H), 5.56 (s, 1H), 5.91 (s, 1H), 6.78 (d, 1H), 7.1 (d, 1H); MS (FAB$^+$): m/z 377.27 (M+H$^+$).

EXAMPLE 13

Preparation of 1-O-Erythritol [2,3-dichloro-4-(2-methylenebutyryl)]phenoxyacetate (Formula XII), with reference to Scheme IX.

Ethacrynic acid (0.46 g, 1.53 mmol) was suspended in benzene (3.0 mL) and thionyl chloride (0.23 mL, 2 equiv) and heated to reflux for 1.5 h. The reaction was cooled to room temperature and concentrated under reduced pressure. The resulting oil was dissolved in DMF (1.0 mL) was added dropwise to a suspension of erythritol (0.44 g, 2 eq) in DMF (3.0 mL). The reaction was heated to 80° C. for 1.5 h, then evaporated under reduced pressure. The crude products were purified by column chromatography (eluting with 15:1 EtOAc/MeOH) to give 1-O-erythritol [2,3-dichloro-4-(2-methylenebutyryl)]phenoxyacetate (0.23 g) as a clear oil that slowly formed a semisolid. IR: 3400, 2967, 1759, 1666, 1585, 1203 cm$^{-1}$; $^1$HNMR (CDCl$_3$, 300 MHz): δ1.10 (t, 3H), 2.40 (q, 2H), 3.70 (m, 3H), 4.2-3.8 (m, 2H), 4.40 (m, 2H), 4.84, (s, 2H), 5.60 (s, 1H), 5.98 (s, 1H), 6.95 (d, 1H), 7.16 (d, 1H); $^{13}$CNMR (CDCl$_3$, 75 MHz): δ12.3, 14.2, 21.0, 23.3, 60.4, 66.8, 70.8, 72.1, 72.5, 111.1, 122.9, 127.0, 129.5, 131.1, 133.6, 149.9, 1553, 1688, 196.4; MS (FAB$^+$): m/z 407 (M+H$^+$).

EXAMPLE 14

Preparation of 1-O-Ribitol [2,3-dichloro-4-(2-methylenebutyryl)]phenoxyacetate (Formula XIII), with reference to Scheme X.

Formula XII

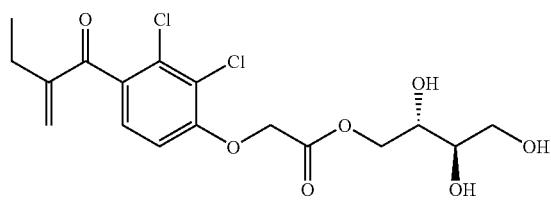

Formula XIII

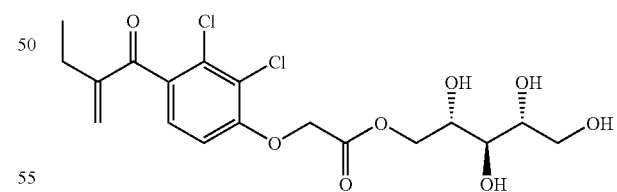

Scheme IX

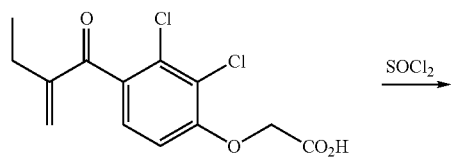

Scheme X

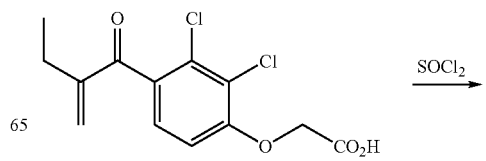

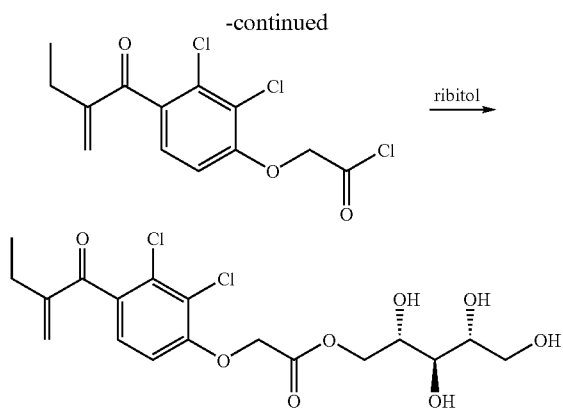

Ethacrynic acid (0.46 g, 1.53 mmol) was suspended in benzene (3.0 mL) and thionyl chloride (0.23 mL, 2 equiv) and heated to reflux for 1.5 h. The reaction was cooled to room temperature and concentrated under reduced pressure. The resulting oil was dissolved in DMF (3.0 mL) and ribitol (0.53 g, 2 equiv) was added. The reaction was allowed to stir at room temperature overnight, then concentrated under reduced pressure. The crude products were purified by column chromatography (eluting with 15:1 EtOAc/MeOH) to give 1-O-ribitol [2,3-dichloro-4-(2-methylenebutyryl)]phenoxyacetate. IR: 3400, 2933, 2940, 1755, 1669, 1585, 1204 cm$^{-1}$; $^1$HNMR (CDCl$_3$, 300 MHz): δ1.10 (t, 3H), 2.40 (q, 2H), 3.70 (m, 3H), 4.2-3.8 (m, 3H), 4.40 (m, 2H), 4.84, (s, 2H), 5.60 (s, 1H), 5.98 (s, 1H), 6.95 (d, 1H), 7.16 (d, 1H); MS (FAB$^+$): m/z 437 (M+H$^+$).

EXAMPLE 15

In order to study the utility of the compounds in the treatment of glaucoma, their effects on intraocular pressure (IOP) were investigated following administration to normotensive rabbits.

Preparation of Eye-Drop Formulations:
  5-O-Ribitol [2,3-dichloro-4-(thiophene-2-carbonyl)]phenoxyacetate: 10% and 15% in a lanolin base.
  5-O-Xylitol 4-(2-phenylacryloyl)cinnamate: 0.3% and 0.6% mixed equimolar with cysteine in solution.
  5-O-{(9α,11α,15R)-15-[2-Benzo[b]thiophen-2-yl]-16,17,18,19,20-pentanor-5,6,13,14-tetrahydro-9,11,15-trihydroxyprostanoyl}xylitol: 0.004% in solution.
  1-O-{(9α,11α,15R)-15-[2-Benzo[b]thiophen-2-yl]-16,17,18,19,20-pentanor-5,6,13,14-tetrahydro-9,11,15-trihydroxyprostanoyl}-11-hydroxy-3,6,9-trioxaundecane: 0.004% and 0.02% in solution.
  11-Hydroxy-3,6,9-trioxaundecyl 4-(2-phenylacryloyl)cinnamate: 0.3% and 0.6% mixed equimolar with cysteine in solution.

Animal Protocol:
  Eyedrops administered topically to male Dutch-belted rabbits (3-5 kg). IOP determinations made with pneumatonometer (Medtronic Solan, Jacksonville, Fla.) as the average of three measurements per eye at each timepoint. Prior to IOP determination and drug administration, eyes were topically anesthetized with proparacaine hydrochloride, 0.5% (Bausch and Lomb, Inc, Tampa, Fla.).

Compounds were Administered According to the Following Protocols:
  5-O-Ribitol [2,3-dichloro-4-(thiophene-2-carbonyl)]phenoxyacetate: Eyedrops containing the compound were administered once a day for three days. The contralateral eye was administered lanolin base. IOP was assessed in the morning and afternoon for seven days.
  5-O-Xylitol 4-(2-phenylacryloyl)cinnamate: Eyedrops containing the compound were administered twice daily for 7 days. The contralateral eye was left untreated to serve as a control. IOP was assessed concurrently with drug administration.
  5-O-{(9α,11α,15R)-15-[2-Benzo[b]thiophen-2-yl]-16,17,18,19,20-pentanor-5,6,13,14-tetrahydro-9,11,15-trihydroxyprostanoyl}xylitol: Eyedrops containing the compound were administered once daily for 7 days. No drug was given on days 8 and 9. The animals were then treated once daily on days 10 through 14. IOP was assessed concurrently with drug administration.
  1-O-{(9α,11α,15R)-15-[2-Benzo[b]thiophen-2-yl]-16,17,18,19,20-pentanor-5,6,13,14-tetrahydro-9,11,15-trihydroxyprostanoyl}-11-hydroxy-3,6,9-trioxaundecane: Eyedrops containing the compound were administered once daily for 5 days. The contralateral eye was left untreated to serve as a control. IOP was assessed concurrently with drug administration.
  11-Hydroxy-3,6,9-trioxaundecyl 4-(2-phenylacryloyl)cinnamate: Eyedrops containing the compound were administered twice daily for 7 days. The contralateral eye was left untreated to serve as a control. IOP was assessed concurrently with drug administration.

Figure 6:
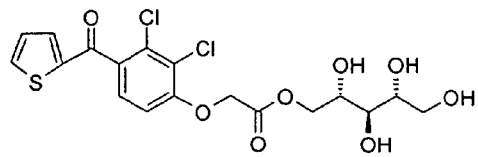
FIG. 6. Measurements of intraocular pressure in rabbits following treatment with 5-O-Ribitol [2,3-dichloro-4-(thiophene-2-carbonyl)]phenoxyacetate (10% and 15% in a lanolin base).
Figure 6:
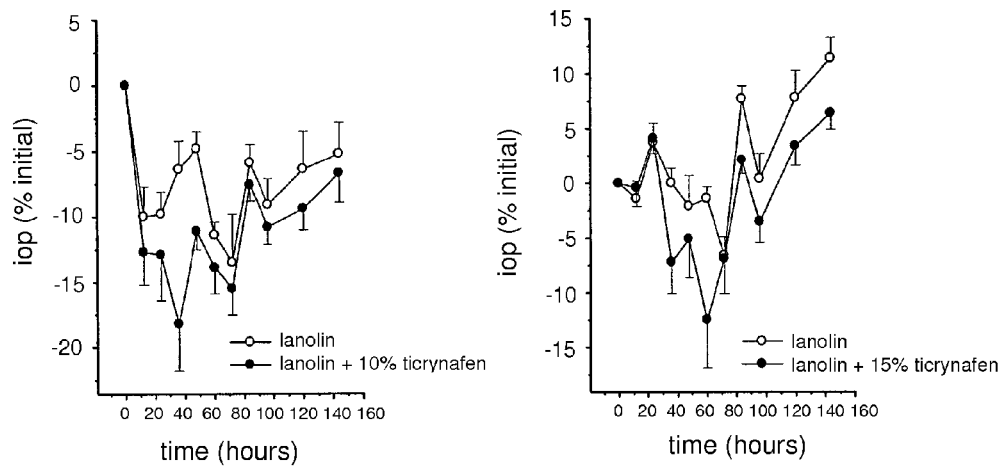
Figure 7:
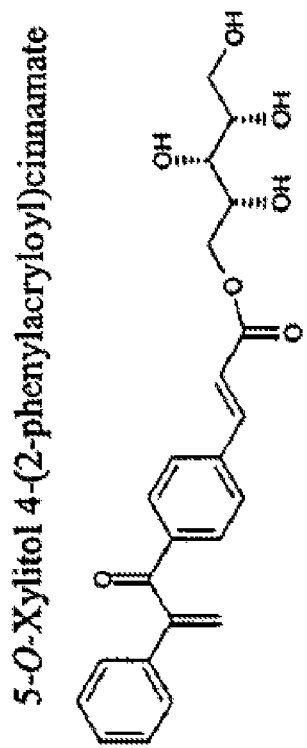
FIG. 7. Measurements of intraocular pressure in rabbits following treatment with 5-O-Xylitol 4-(2-phenylacryloyl)cinnamate (0.3% and 0.6% mixed equimolar with cysteine in solution).
Figure 7:
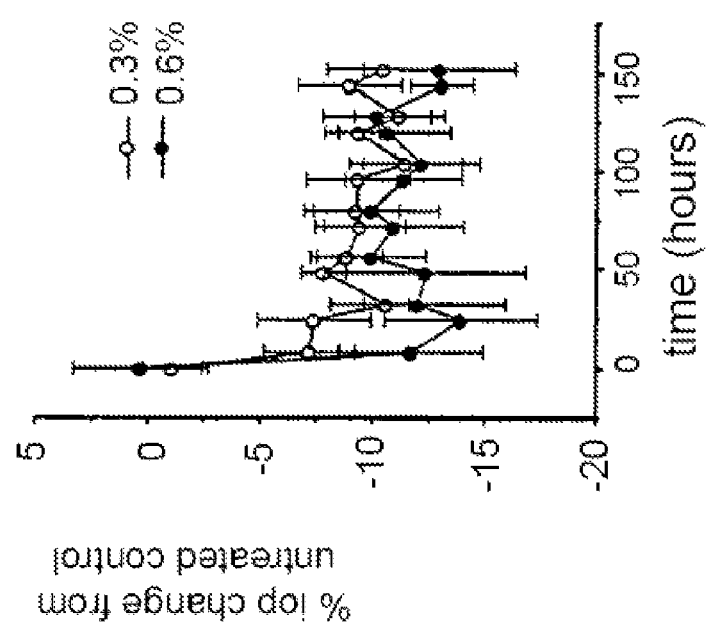
Figure 8:
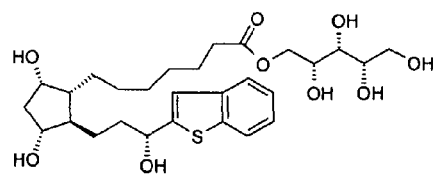
FIG. 8. Measurements of intraocular pressure in rabbits following treatment with 5-O-{(9α,11α,15R)-15-[2-Benzo[b]thiophen-2-yl]-16,17,18,19,20-pentanor-5,6,13,14-tetrahydro-9,11,15-trihydroxyprostanoyl}xylitol (0.004% in solution).
Figure 8:
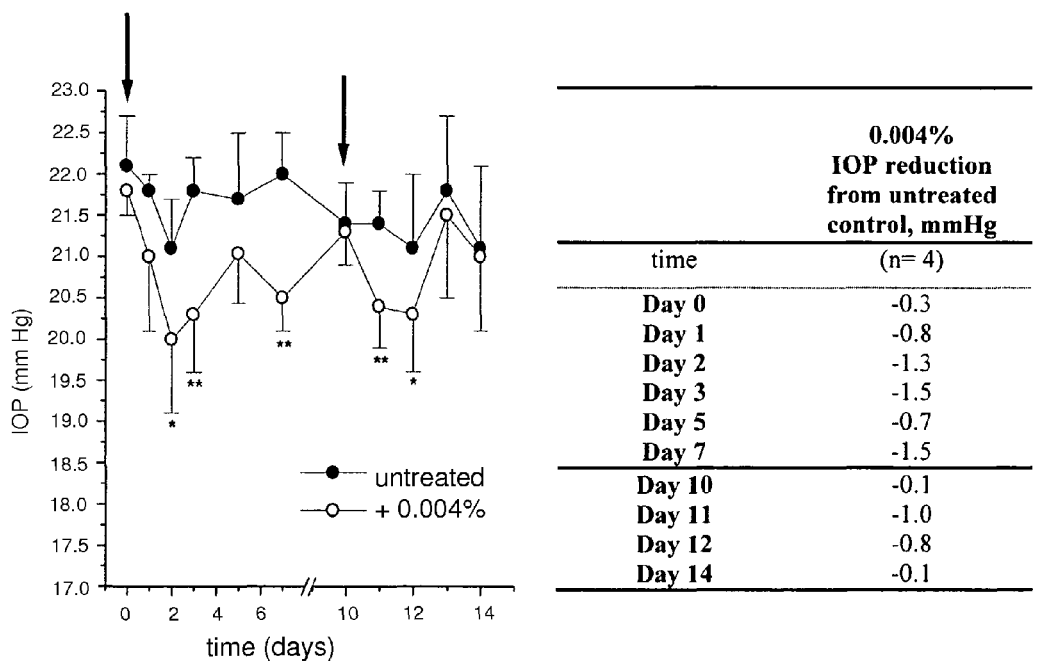
Figure 9:
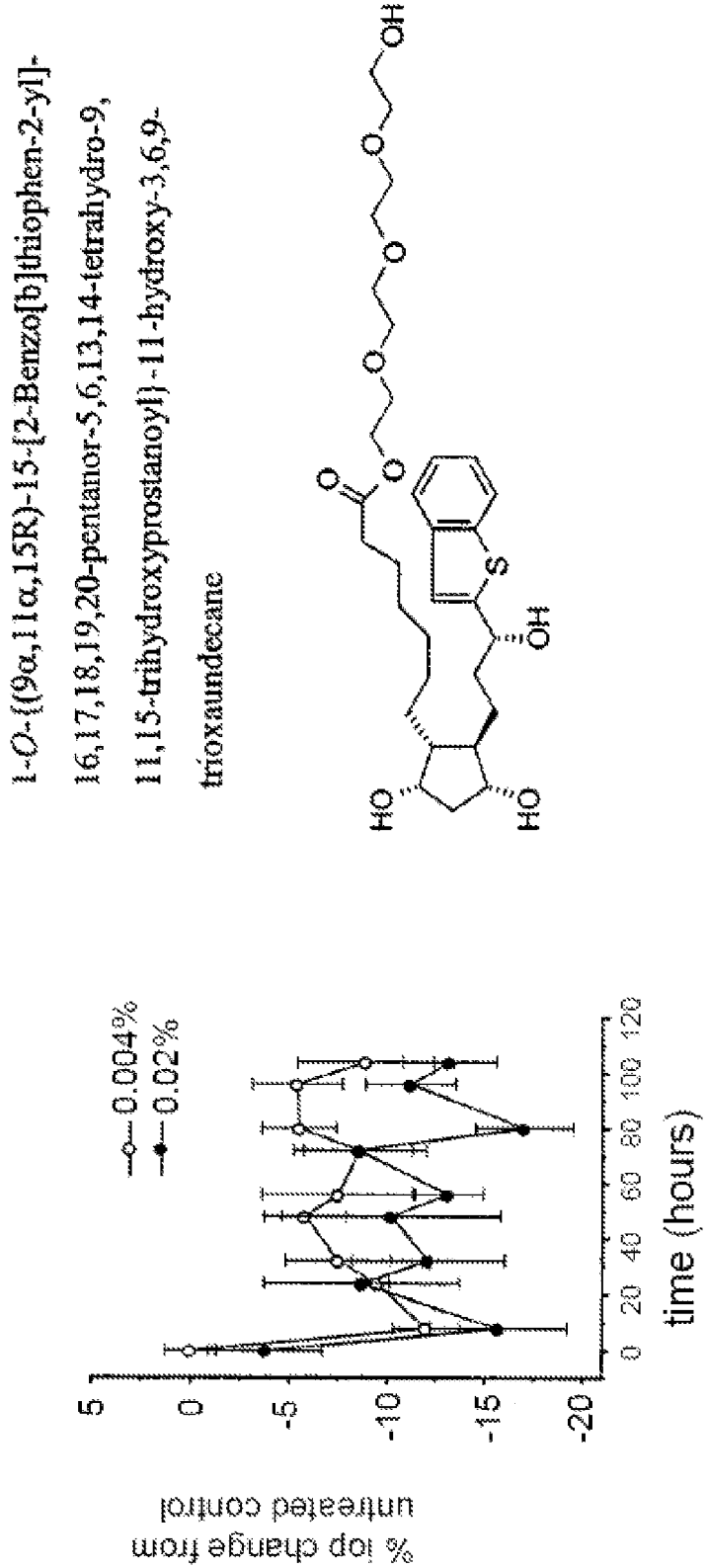
FIG. 9. Measurements of intraocular pressure in rabbits following treatment with 1-O-{(9α,11α,15R)-15-[2-Benzo[b]thiophen-2-yl]-16,17,18,19,20-pentanor-5,6,13,14-tetrahydro-9,11,15-trihydroxyprostanoyl}-11-hydroxy-3,6,9-trioxaundecane (0.004% and 0.02% in solution).
Figure 10:
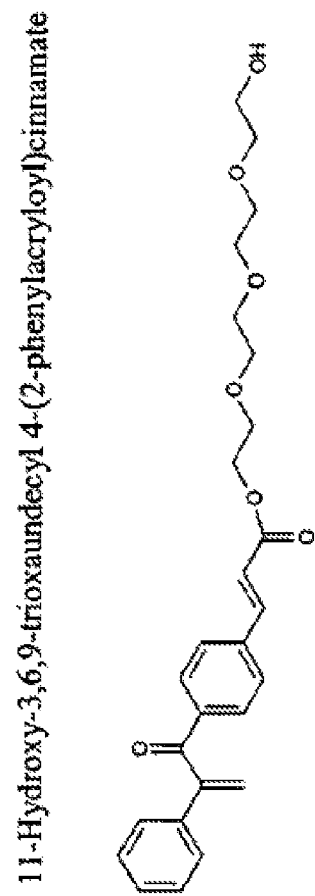
FIG. 10. Measurements of intraocular pressure in rabbits following treatment with 11-Hydroxy-3,6,9-trioxaundecyl 4-(2-phenylacryloyl)cinnamate (0.3% and 0.6% mixed equimolar with cysteine in solution).
Figure 10:
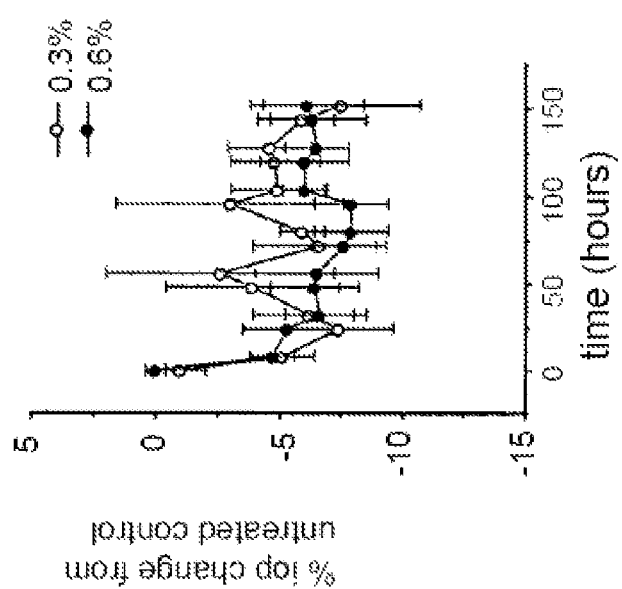

Results:
  5-O-Ribitol [2,3-dichloro-4-(thiophene-2-carbonyl)]phenoxyacetate (FIG. 6):
  Maximum reduction (10%): −4.3 (18%) at 36 hours, (−1.5 for control)
  Maximum reduction (15%): −3.0 (13%) at 60 hours (−0.3 for control)
  5-O-Xylitol 4-(2-phenylacryloyl)cinnamate (FIG. 7):
  Maximum reduction from untreated control (0.3%): −2.4 (11%) mmHg
  Maximum reduction from untreated control (0.6%): −2.4 (13%) mmHg
  5-O-{(9α,11α,15R)-15-[2-Benzo[b]thiophen-2-yl]-16,17,18,19,20-pentanor-5,6,13,14-tetrahydro-9,11,15-trihydroxyprostanoyl}xylitol (FIG. 8)—Significant reductions from baseline on days 2, 3, 5, 11, and 12. Significant reductions from baseline and untreated control on days 3, 5, and 11.
  1-O-{(9α,11α,15R)-15-[2-Benzo[b]thiophen-2-yl]-16,17,18,19,20-pentanor-5,6,13,14-tetrahydro-9,11,15-trihydroxyprostanoyl}-11-hydroxy-3,6,9-trioxaundecane (FIG. 9):
  Maximum reduction from untreated control (0.004%): −2.8 (12%) mmHg
  Maximum reduction from untreated control (0.02%): −3.0 (17%) mmHg
  11-Hydroxy-3,6,9-trioxaundecyl 4-(2-phenylacryloyl)cinnamate (FIG. 10):
  Maximum reduction from untreated control (0.3%): −1.7 (8%) mmHg
  Maximum reduction from untreated control (0.6%): −1.9 (8%) mmHg

EXAMPLE 16

Preparation of the 2-threitol ester of ticrynafen

Using the acid chloride of ticrynafen (shown in Scheme I) and substantially the same conditions as in Example One, but substituting the 1,4-bis-TBDMS-threitol in place of the diacetone ribitol, and limiting the ratio of acid chloride and alcohol to a 1:1 ratio, the coupling of the acid and the secondary alcohol are effected. The crude material is isolated and purified in the same manner as in Example I, and is further treated with TBAF to remove the silyl groups protecting the primary alcohols by the removal method of Example IV. Such manipulations are well-known to one skilled in the art. After purification, again following Example 1,2-O-ticrynafyl threitol is isolated.

EXAMPLE 17

Preparation of the 1-(2-deoxythreitol) ester of ticrynafen

Using the acid chloride of ticrynafen (shown in Scheme I) and substantially the same conditions as in Example I, but substituting the 2-deoxy-3,4-bis silyl threitol (1,3,4 butane triol), readily prepared for example from 1-buten-4-ol by e.g., epoxidation ring opening, in place of the diacetone ribitol, the coupling of the acid and the deoxyalcohol are effected. The crude material is isolated and purified in the same manner as in Example I, and is further treated with TBAF to remove the silyl groups protecting the other alcohols by the removal method of Example IV. Such manipulations are well-known to one skilled in the art. After purification, again following Example I, 1-O-ticrynafyl-1,3,4-trihydroxybutane is isolated.

EXAMPLE 18

Testing the release rate of the 1-(2-deoxythreitol) ester of ticrynafen

Commercially available carboxylic-ester hydrolase (CAS# 9016-18-6) is prepared in suspension as described in C. Tamm *Pure Appl. Chem.* 64, 1187, (1992) and M. Ohno, M. Otsuka *Org. React.* 37, 1, (1989), incorporated herein as reference. The activity is standardized against a reference activity of 1 U corresponds to the amount of enzyme which hydrolyzes 1 micromol ethyl butyrate per minute at pH 8.0 and 25° C. The 1-(2-deoxythreitol) ester of ticrynafen, from Example 8 above, is dissolved in methanol and added dropwise to the stirred solution. The progress of the reaction is followed by TLC using pure ticrynafen as a reference standard. After 5 minutes, and again at doubling intervals the progress of the reaction is followed until there remains no further change in the TLC. A relative rate is determined and compared against the rate needed to ensure corneal penetration and hydrolysis for the disease in question.

The invention claimed is:

1. A method of reducing intraocular pressure, the method comprising administering to a human or other animal a safe and effective amount of a compound derived from the esterification of a carboxylate functionality of a drug moiety with a sugar alcohol selected from the group consisting of threitol, erythritol, arabinitol, xylitol, ribitol, lyxitol, glucitol, galactitol, mannitol, gulitol, altitol, allitol, iditol, talitol, 2-deoxyribitol, 2-deoxyglucitol, 2-deoxyxylitol, and a mixture thereof, the drug moiety comprising at least one of a phenoxyacetic acid, a cinnamic acid, and a mixture thereof, or a pharmaceutically acceptable salt thereof, and a pharmaceutically acceptable carrier.

2. The method of claim 1, wherein the phenoxyacetic acid is selected from the group consisting of ticrynafen, ethacrynic acid, and a mixture thereof.

3. The method of claim 1, wherein the pharmaceutically acceptable carrier is selected from the group consisting of a liquid, gel, cream, and ointment.

4. The method of claim 1, wherein the carrier comprises a physiological saline solution.

5. The method of claim 4, wherein the saline solution is maintained at a pH between 4.5 and 8.0.

6. The method of claim 1, wherein the composition further comprises at least one of a pharmaceutically-acceptable preservative, stabilizer and surfactant.

7. The method of claim 1, wherein the drug moiety comprises a phenoxyacetic acid and the phenoxyacetic acid is ticrynafen.

8. The method of claim 1, wherein the drug moiety comprises a phenoxyacetic acid and the phenoxyacetic acid is ethacrynic acid.

9. The method of claim 1, wherein the drug moiety comprises cinnamic acid.

10. A method of reducing intraocular pressure, the method comprising administering to a human or other animal a safe and effective amount of a compound derived from the esterification of a carboxylate functionality of a drug moiety with a sugar alcohol selected from the group consisting of threitol, erythritol, arabinitol, xylitol, ribitol, lyxitol, glucitol, galactitol, mannitol, gulitol, altitol, allitol, iditol, talitol, and a mixture thereof, the drug moiety comprising at least one of a phenoxyacetic acid, a cinnamic acid, and a mixture thereof, or a pharmaceutically acceptable salt thereof, and a pharmaceutically acceptable carrier.

11. The method of claim 10, wherein the drug moiety comprises a phenoxyacetic acid and the phenoxyacetic acid is selected from the group consisting of ticrynafen, ethacrynic acid, and a mixture thereof.

12. The method of claim 10, wherein the drug moiety comprises a phenoxyacetic acid and the phenoxyacetic acid is ticrynafen.

13. The method of claim 10, wherein the drug moiety comprises a phenoxyacetic acid and the phenoxyacetic acid is ethacrynic acid.

14. The method of claim 10, wherein the drug moiety comprises cinnamic acid.

15. The method of claim 10, wherein the composition further comprises at least one of a pharmaceutically-acceptable preservative, stabilizer and surfactant.

16. The method of claim 10, wherein the pharmaceutically acceptable carrier is selected from the group consisting of a liquid, gel, cream, and ointment.

17. The method of claim 10, wherein the pharmaceutically acceptable carrier is selected from the group consisting of a saline solution, gel, cream, and ointment.

18. A method of reducing intraocular pressure, the method comprising administering to a human or other animal a safe and effective amount of a compound derived from the esterification of a carboxylate functionality of a drug moiety with a sugar alcohol selected from the group consisting of threitol, erythritol, arabinitol, xylitol, ribitol, lyxitol, glucitol, galactitol, gulitol, altitol, allitol, iditol, talitol, 2-deoxyribitol, 2-deoxyglucitol, 2-deoxyxylitol, and a mixture thereof, the drug moiety comprising at least one of a phenoxyacetic acid, a cinnamic acid, and a mixture thereof, or a pharmaceutically acceptable salt thereof, and a pharmaceutically acceptable carrier.

19. The method of claim 18, wherein the drug moiety comprises a phenoxyacetic acid and the phenoxyacetic acid is selected from the group consisting of ticrynafen, ethacrynic acid, and a mixture thereof.

20. The method of claim 18, wherein the drug moiety comprises a phenoxyacetic acid and the phenoxyacetic acid is ticrynafen.

21. The method of claim 18, wherein the drug moiety comprises a phenoxyacetic acid and the phenoxyacetic acid is ethacrynic acid.

22. The method of claim 18, wherein the drug moiety comprises cinnamic acid.

23. The method of claim 18, wherein the composition further comprises at least one of a pharmaceutically-acceptable preservative, stabilizer and surfactant.

24. The method of claim 18, wherein the pharmaceutically acceptable carrier comprises an ophthalmically acceptable pharmaceutical excipient.

25. The method of claim 18, wherein the pharmaceutically acceptable carrier is selected from the group consisting of a liquid, gel, cream, and ointment.

* * * * *